(12) United States Patent
Kalhor et al.

(10) Patent No.: US 10,745,814 B2
(45) Date of Patent: Aug. 18, 2020

(54) ENZYMATIC NUCLEIC ACID SYNTHESIS

(71) Applicant: President and Fellows of Harvard College, Cambridge, MA (US)

(72) Inventors: Reza Kalhor, East Boston, MA (US); Henry Hung-yi Lee, Brookline, MA (US); George M. Church, Brookline, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 77 days.

(21) Appl. No.: 16/099,487

(22) PCT Filed: May 9, 2017

(86) PCT No.: PCT/US2017/031658
§ 371 (c)(1),
(2) Date: Nov. 7, 2018

(87) PCT Pub. No.: WO2017/196783
PCT Pub. Date: Nov. 16, 2017

(65) Prior Publication Data
US 2019/0145013 A1 May 16, 2019

Related U.S. Application Data

(60) Provisional application No. 62/333,501, filed on May 9, 2016.

(51) Int. Cl.
| | | |
|---|---|---|
| *C25B 3/10* | (2006.01) | |
| *C12Q 1/6844* | (2018.01) | |
| *C12P 19/34* | (2006.01) | |
| *C25B 3/02* | (2006.01) | |
| *C25B 3/04* | (2006.01) | |
| *C12Q 1/6806* | (2018.01) | |

(52) U.S. Cl.
CPC .............. *C25B 3/10* (2013.01); *C12P 19/34* (2013.01); *C12Q 1/6844* (2013.01); *C25B 3/02* (2013.01); *C25B 3/04* (2013.01); *B01J 2219/00653* (2013.01); *B01J 2219/00713* (2013.01); *B01J 2219/00722* (2013.01); *C12Q 1/6806* (2013.01)

(58) Field of Classification Search
CPC .............................. C12Q 1/6844; C12P 29/34
See application file for complete search history.

(56) References Cited

U.S. PATENT DOCUMENTS

| | | | |
|---|---|---|---|
| 5,942,609 A | 8/1999 | Hunkapiller et al. | |
| 6,051,380 A * | 4/2000 | Sosnowski | B01J 19/0046 435/6.11 |
| 8,603,803 B2 * | 12/2013 | Wang | G01N 27/226 205/122 |
| 2006/0275927 A1 * | 12/2006 | Dubin | B01J 19/0046 438/1 |
| 2009/0134042 A1 | 5/2009 | Nomoto et al. | |
| 2012/0279874 A1 | 11/2012 | Lawrence et al. | |
| 2014/0120521 A1 | 5/2014 | Abi-Samra et al. | |
| 2014/0127702 A1 | 5/2014 | Wang et al. | |
| 2014/0206550 A1 | 7/2014 | Bjornson et al. | |
| 2016/0186166 A1 * | 6/2016 | Poehmerer | B03C 5/026 205/420 |
| 2019/0040459 A1 | 2/2019 | Efcavitch et al. | |

* cited by examiner

Primary Examiner — Narayan K Bhat
(74) Attorney, Agent, or Firm — Banner & Witcoff, Ltd.

(57) ABSTRACT

The present disclosure provides methods of activating an enzyme, such as error prone or template independent polymerase, using electricity to alter pH of a reaction zone and reaction site from an inactivating pH at which the enzyme is inactive to an activating pH at which the enzyme is active to add a nucleotide to an initiator or growing polymer chain. The activating pH can then be changed back to an inactivating pH and the process repeated as many times as desired to produce a target nucleic acid sequence.

48 Claims, 9 Drawing Sheets

Specification includes a Sequence Listing.

7-Deaza-7-bromo-dATP

7-Deaza-7-iodo-dATP

5-Bromo-dUTP

5-Iodo-dUTP

Alpha Thiol dGTP

Alpha Thiol dATP

Beta Thiol dGTP

Beta Thiol dATP

Lanes in order: pH=6, 7, 8, 9, 10, 11, non-extended initiator.

B = A, T, C, G

X = thermolabile group, where OX =

Tetrahydropyranyl (THP)  4-Methoxy-tetrahydropyranyl (MTHP)  Tetrahydrofuranyl (THF)  Acetyl (Ac)  Methoxyacetyl (Mac)  Phenoxyacetyl (Pac)

Trityl ethers

DMT, Z = H
TMT, Z = Me

Pixyl

THP and THF ethers

THP

MTHP

MSTHP

THF

MeTHF

1-substituted Ethyl ethers

R

EE

CHE

TBE

IBE

TPE

SEQUENCE LISTING

```
<160> NUMBER OF SEQ ID NOS: 2

<210> SEQ ID NO 1
<211> LENGTH: 34
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 1
ttttuctaca ctctttccct acacgacgct cttc                               34

<210> SEQ ID NO 2
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
cagtcagatc ggaagagcac acgtctgaac tccagtca                           38
```

ENZYMATIC NUCLEIC ACID SYNTHESIS

RELATED APPLICATIONS

This application is a National Stage Application under 35 U.S.C. 371 of co-pending PCT application PCT/US17/31658 designating the United States and filed May 9, 2017; which claims the benefit of U.S. provisional application No. 62/333,501 filed on May 9, 2016 each of which are hereby incorporated by reference in their entireties.

STATEMENT OF GOVERNMENT INTERESTS

This invention was made with government support under Grant No. 1R01MH103910-01 awarded by National Institutes of Health. The government has certain rights in the invention.

FIELD

The present invention relates in general to methods of making oligonucleotides and polynucleotides using enzymatic synthesis.

BACKGROUND

DNA has been proposed as a highly desirable medium for storage of digital information. The barrier to such use of DNA is the low efficiency and speed as well as the high cost of current synthesis methods. In the current state of the art, DNA is synthesized using phosphoramidite precursors in organic solvents. These chemical synthesis methods result in errors of approximately 1% and take approximately 10 minutes per addition step. Furthermore, the reagents that are used in this synthesis process are expensive. Some of these same reagents also damage DNA, a problem that precludes the possibility of synthesizing DNA strands that are longer than ~200 bases, further hampering the efficiency of this chemical process. TdT is currently used in batch reactions for the addition of variable lengths of singular nucleotides or uncontrolled sequence of nucleotide mixtures to the 3' end of a nucleic acid sequence. A need remains for the development of faster and cheaper enzymatic oligonucleotide synthesis methods than the existing chemical oligonucleotide synthesis methods.

SUMMARY

The present disclosure is directed to the use of an electric current to generate a pH within a reaction zone that activates an enzyme, such as an error prone or template independent polymerase, to add a nucleotide, such as a nucleotide triphosphate, to an initiator. This method allows the production of one or more polynucleotides using enzymatic polymer synthesis. For example, an enzyme such as terminal deoxynucleotidyl transferase (TdT) (which extends single stranded nucleic acid templates with nucleotide triphosphates without use of a template) is combined with one or more nucleotide triphosphates such as A, C, G or T/U (dATP, dCTP, dGTP, dTTP, dUTP) or non-naturally occurring or synthetic nucleotide triphosphates and other reagents under pH conditions where the enzyme is inactive. An electric current is used to alter pH at the reaction site within the reaction zone to activate the enzyme to add one or more nucleotide triphosphates to an initiator sequence or growing nucleic acid sequence. A plurality of reactions may be carried out in parallel to produce a plurality of nucleic acids using separate voltages applied to different reaction sites. The present disclosure provides sequential exposure of nucleic acids to different nucleotides to obtain nucleic acid polymers of a desired sequence.

The methods according to the present disclosure can be used for synthesis of cheaper, more accurate and longer custom DNA sequences for various biochemical, biomedical, or biosynthetic applications. Furthermore, given the potential for high-speed DNA synthesis, the methods according to the present disclosure can facilitate the use of DNA as an information storage medium. In this case, a solid-phase synthesis device can be used to record digital information in DNA molecules.

Further features and advantages of certain embodiments of the present invention will become more fully apparent in the following description of embodiments and drawings thereof, and from the claims.

BRIEF DESCRIPTION OF THE DRAWINGS

The foregoing and other features and advantages of the present embodiments will be more fully understood from the following detailed description of illustrative embodiments taken in conjunction with the accompanying drawings in which.

DETAILED DESCRIPTION

Figure 1:
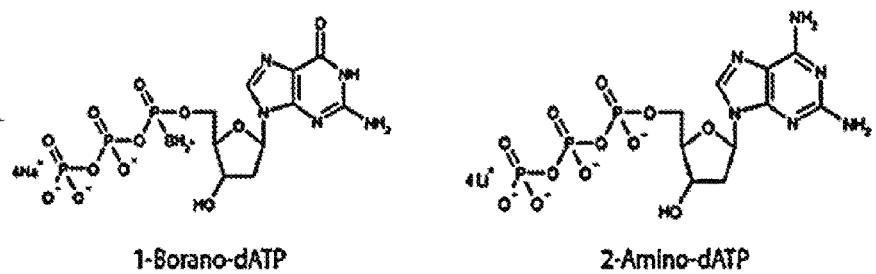
FIG. 1 depicts screened nucleotide analog substrates for TdT to select for better performance on extension efficiency, rate, and extension length distribution according to the embodiments of the disclosed methods.
Figure 1:
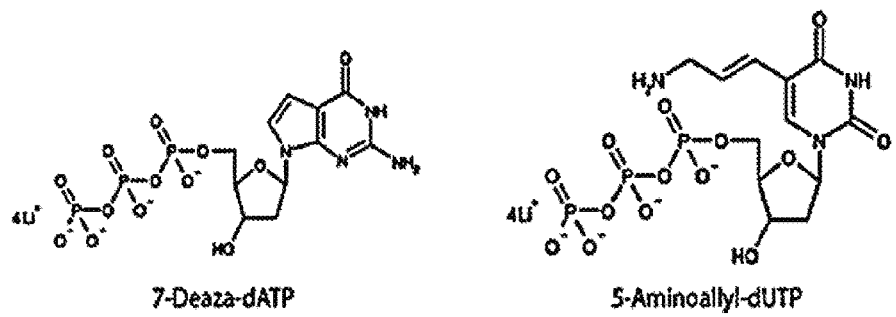
Figure 1:
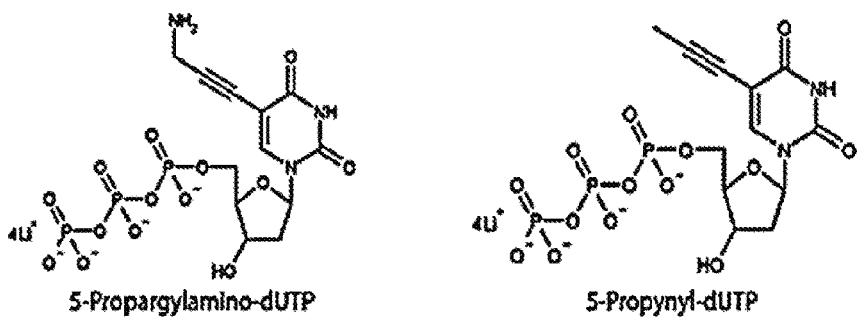
Figure 1:
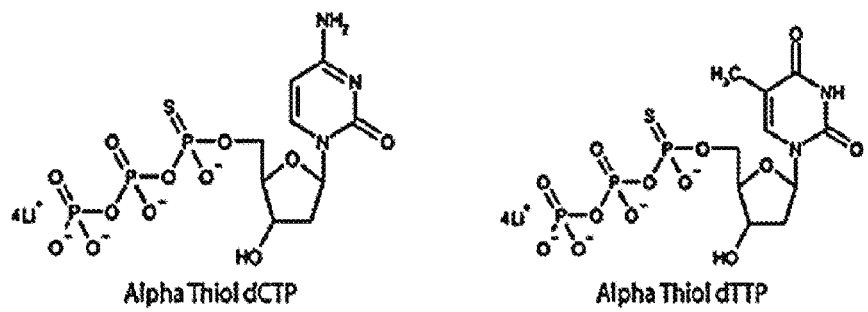
Figure 1:
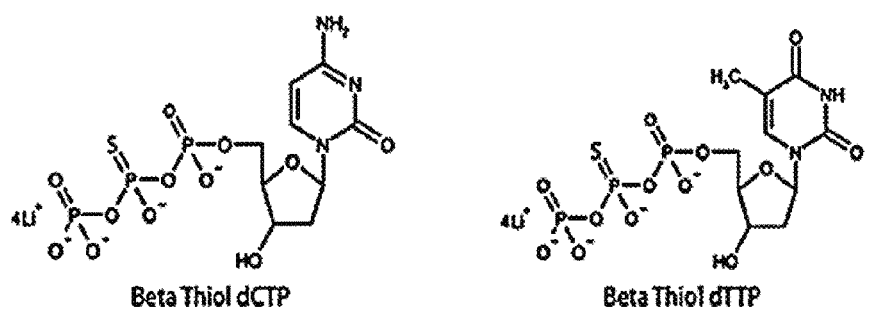
Figure 1:
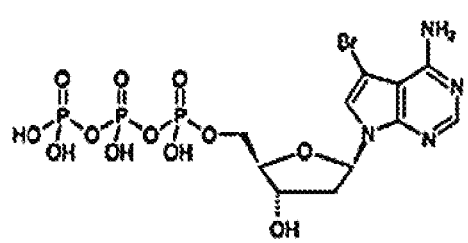
Figure 1:
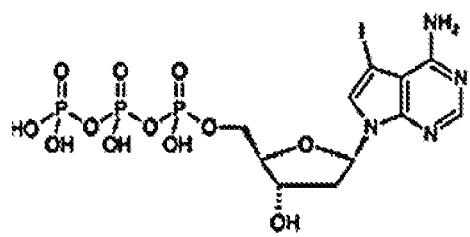
Figure 1:
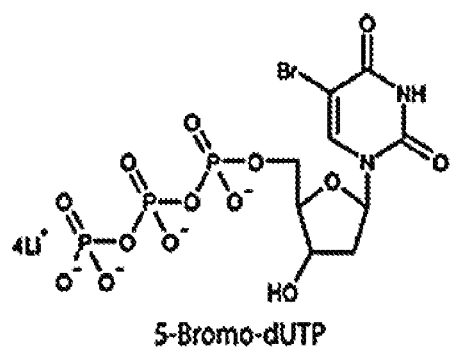
Figure 1:
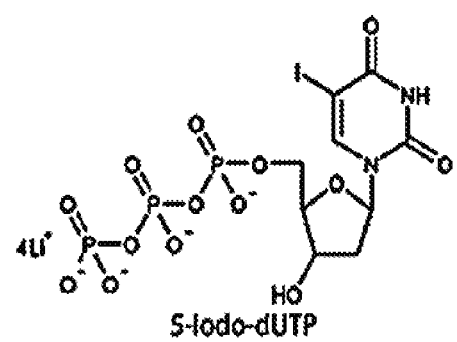
Figure 1:
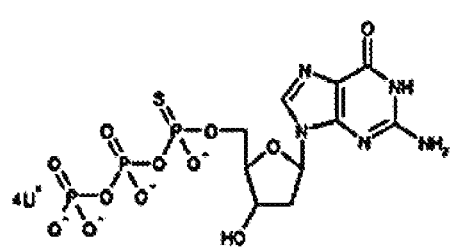
Figure 1:
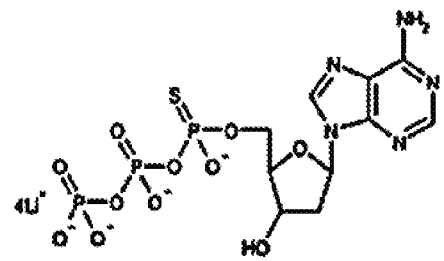
Figure 1:
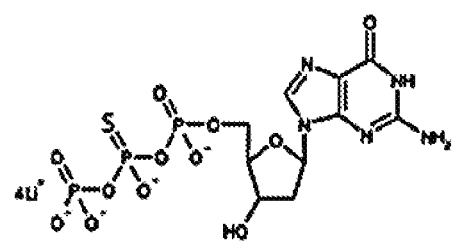
Figure 1:
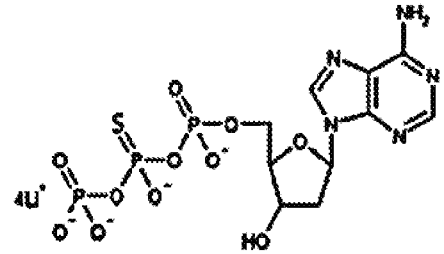

The present disclosure provides methods of activating an enzyme, such as error prone or template independent polymerase, using electricity to alter pH of a reaction zone and reaction site from an inactivating pH at which the enzyme is inactive to an activating pH at which the enzyme is active. The activating pH can then be changed back to an inactivating pH and the process repeated as many times as desired to produce a target nucleic acid sequence. The pH can be altered or regulated to change the reaction zone from one which activates the enzyme to one which inactivates the enzyme in a manner to regulate the addition of a nucleotide to an initiator or primer or nucleic acid or growing nucleic acid oligomer or polymer. In this manner, nucleotide addition can be controlled to a desired number of nucleotides, such as one nucleotide, two nucleotides, three nucleotides etc. The disclosure provides that addition is limited to one nucleotide, two nucleotides, three nucleotides or more during one round of nucleotide addition. This activation or inactivation of the enzyme through regulation of pH using electricity allows for multiple rounds of nucleotide polymerization where a different nucleotide is added to the initiator or primer or nucleic acid or growing nucleic acid oligomer or polymer.

The present disclosure provides methods of enzymatic synthesis using electricity to generate oxidation or reduction reactions to regulate pH in an aqueous electrolyte that activates or deactivates enzymatic nucleic acid synthesis. Regulating pH enables control over the number and nature of nucleotides that an error prone or template independent polymerase such as TdT adds to a primer strand of DNA, i.e., the primer/initiator for DNA synthesis. Exemplary embodiments of the present disclosure are directed to methods of enzymatic synthesis of user-defined nucleic acid sequences using TdT. Methods according to the present disclosure can be used for the synthesis of nucleic acid polymers for information storage in DNA. Methods according to the present disclosure further provide improved control of the number and nature of nucleotides that template-independent DNA polymerases, such as TdT, incorporate into nucleic acid polymers and enable user-defined synthesis of nucleic acid sequences useful for biological applications.

According to certain aspects of the present disclosure, the methods involve a reaction site and a fluidic/microfluidic device which may be computer controlled to provide and remove one or more reaction reagents or buffers to the reaction site (or a plurality of reaction sites) wherein initiator oligonucleotides (nucleic acids that act as the initial substrate for an enzyme such as TdT to extend with the desired sequence) are immobilized on or at the reaction site. One electrode of an electrochemical cell is at or near or adjacent the reaction site. After combination of suitable reaction reagents at the reaction site, applying voltage to the electrochemical cell results in oxidation or reduction which may either raise or lower initial pH within a reaction zone which includes the reaction site. The raising or lowering of pH may activate or inactivate the enzyme.

The disclosure provides for the use of natural dNTPs, non-natural dNTPs, dNTP analogues, synthetic dNTPs or reversible terminator dNTPs. Terminator dNTPs are modified dNTPs that TdT can add to a growing DNA primer but cannot extend further. In such a system, after each reversible terminator dNTP is added, a reagent is added or other stimulus is applied that reverts the termination chemically, physically, or enzymatically, followed by the next desired reversible terminator dNTP, and so on.

Polymerases, including without limitation error-prone or template-dependent polymerases, modified or otherwise, can be used to create nucleotide polymers having a random or known or desired sequence of nucleotides. Template-independent polymerases, whether modified or otherwise, can be used to create the nucleic acids de novo. Ordinary nucleotides are used, such as A, T/U, C or G. Nucleotides may be used which lack chain terminating moieties. Reversible terminators may be used in the methods of making the nucleotide polymers. A template independent polymerase may be used to make the nucleic acid sequence. Such template independent polymerase may be error-prone which may lead to the addition of more than one nucleotide resulting in a homopolymer.

Oligonucleotide sequences or polynucleotide sequences are synthesized using an error prone polymerase, such as a template independent error prone polymerase, and common or natural nucleic acids, which may be unmodified. Initiator sequences or primers are attached to a substrate, such as a silicon dioxide substrate, at various locations whether known, such as in an addressable array, or random. Reagents including at least a selected nucleotide, a template independent polymerase and other reagents required for enzymatic activity of the polymerase are applied at one or more locations of the substrate where the initiator sequences are located and under pH conditions where the polymerase adds one or more than one or a plurality of the nucleotide to the initiator sequence to extend the initiator sequence. The initial pH may be an inactivating pH at which the polymerase is inactive. The initial inactivating pH is altered to an activating pH at which the polymerase is active. Polymerase activity can be controlled by pH. It is well known in the art that each polymerase has an active pH range outside of which it is inactive. In one embodiment, the reaction reagent pH can be adjusted in and out of the active range to control the polymerase. In an exemplary embodiment, it has been determined that TdT is active below pH 10 but is inactive at pH 11. Therefore, if the initial setup of the reaction is at pH 11, temporarily changing the pH to anywhere below 10 can temporarily activate the TdT enzyme.

The nucleotides ("dNTPs") may be applied or flowed to the reaction site in periodic applications. Nucleotides with blocking groups or reversible terminators can be used with the dNTPs under reaction conditions that are sufficient to limit or reduce the probability of enzymatic addition of the dNTP to one dNTP, i.e. one dNTP is added using the selected reaction conditions taking into consideration the reaction kinetics. Nucleotides with blocking groups or reversible terminators are known to those of skill in the art. According to an additional embodiment when reaction conditions permit, more than one dNTP may be added to form a homopolymer run when common or natural nucleotides are used with a template independent error prone polymerase.

Polymerase activity may be modified using electrochemical modulation as a reaction condition so as to activate or deactivate the polymerase to add a dNTP or minimize addition of dNTP beyond a single dNTP. The disclosure provides for the use of an electrode of an electrochemical cell or other conductive element within a suitable environment and an applied voltage to produce either an oxidation or reduction reaction altering pH to either activate or deactivate the polymerase. One or more reaction reagents present at the reaction site or within the reaction zone may be removed from the reaction site or from within the reaction region and one or more reaction reagents may be introduced to the reaction site or within the reaction zone. A wash may be applied to the one or more locations or reaction sites or reaction zones to remove the one or more reagents. The steps of applying the reagents are repeated until desired nucleic acids are created. According to one aspect, the reagents may be added or deposited to one or more than one or a plurality of locations on the substrate in series or in parallel according to methods known to those of skill in the art such as depositing, flowing, spotting, spraying etc., or the reagents may contact the entire surface of the support, such as by flowing the reagents across the surface of the support.

A flow cell or other channel, such a microfluidic channel or microfluidic channels having an input and an output may be used to deliver reaction fluids including reagents, such as a polymerase, a nucleotide and other appropriate reagents and washes to particular locations on a substrate or reaction site. The substrate or reaction site may be within the flow cell, such as within a microfluidic channel, or within a separate reaction chamber including the reaction site, the reaction zone and the electrode or other conductive structure or other structure which can generate oxidation or reduction reactions for altering pH between an inactivating pH and an activating pH. One of skill will recognize that reaction conditions will be based on dimensions of the substrate reaction region, reagents, concentrations, reaction temperature, and the structures used to create and deliver the reagents and washes. According to certain aspects, pH and other reactants and reaction conditions can be optimized for the use of TdT to add a dNTP to an existing nucleotide or oligonucleotide in a template independent manner. For example, Ashley et al., Virology 77, 367-375 (1977) hereby incorporated by reference in its entirety identifies certain reagents and reaction conditions for dNTP addition, such as initiator size, divalent cation and pH. TdT was reported to be active over a wide pH range with an optimal pH of 6.85. Methods of providing or delivering dNTP, rNTP or rNDP are useful in making nucleic acids.

Terms and symbols of nucleic acid chemistry, biochemistry, genetics, and molecular biology used herein follow those of standard treatises and texts in the field, e.g., Kornberg and Baker, DNA Replication, Second Edition (W.H. Freeman, New York, 1992); Lehninger, Biochemistry, Second Edition (Worth Publishers, New York, 1975); Strachan and Read, Human Molecular Genetics, Second Edition (Wiley-Liss, New York, 1999); Eckstein, editor, Oligonucleotides and Analogs: A Practical Approach (Oxford University Press, New York, 1991); Gait, editor, Oligonucleotide Synthesis: A Practical Approach (IRL Press, Oxford, 1984); and the like.

Polymerases

The present disclosure provides for the use of polymerases to build nucleic acid molecules, such as for representing information which is referred to herein as being recorded in the nucleic acid sequence or the nucleic acid is referred to herein as being storage media. Polymerases are enzymes that produce a nucleic acid sequence, for example, using DNA or RNA as a template. Polymerases that produce RNA polymers are known as RNA polymerases, while polymerases that produce DNA polymers are known as DNA polymerases. Polymerases that incorporate errors are known in the art and are referred to herein as "error-prone polymerases". Template independent polymerases may be error prone polymerases. Using an error-prone polymerase allows the incorporation of specific bases at precise locations of the DNA molecule. Error-prone polymerases will either accept a non-standard base, such as a reversible chain terminating base, or will incorporate a different nucleotide, such as a natural or unmodified nucleotide that is selectively given to it as it tries to copy a template. Template-independent polymerases such as terminal deoxynucleotidyl transferase (TdT), also known as DNA nucleotidylexotransferase (DNTT) or terminal transferase create nucleic acid strands by catalyzing the addition of nucleotides to the 3' terminus of a DNA molecule without a template. The preferred substrate of TdT is a 3'-overhang, but it can also add nucleotides to blunt or recessed 3' ends. Cobalt is a cofactor, however the enzyme catalyzes reaction upon Mg and Mn administration in vitro. Nucleic acid initiators may be 4 or 5 nucleotides or longer and may be single stranded or double stranded. Double stranded initiators may have a 3' overhang or they may be blunt ended or they may have a 3' recessed end.

TdT, like all DNA polymerases, also requires divalent metal ions for catalysis. However, TdT is unique in its ability to use a variety of divalent cations such as $Co^{2+}$, $Mn^{2+}$, $Zn^{2+}$ and $Mg^{2+}$. In general, the extension rate of the primer p(dA)n (where n is the chain length from 4 through 50) with dATP in the presence of divalent metal ions is ranked in the following order: $Mg^{2+}>Zn^{2+}>Co^{2+}>Mn^{2+}$. In addition, each metal ion has different effects on the kinetics of nucleotide incorporation. For example, $Mg^{2+}$ facilitates the preferential utilization of dGTP and dATP whereas $Co^{2+}$ increases the catalytic polymerization efficiency of the pyrimidines, dCTP and dTTP $Zn^{2+}$ behaves as a unique positive effector for TdT since reaction rates with $Mg^{2+}$ are stimulated by the addition of micromolar quantities of $Zn^{2+}$. This enhancement may reflect the ability of $Zn^{2+}$ to induce conformational changes in TdT that yields higher catalytic efficiencies. Polymerization rates are lower in the presence of $Mn^{2+}$ compared to $Mg^{2+}$, suggesting that $Mn^{2+}$ does not support the reaction as efficiently as $Mg^{2+}$. Further description of TdT is provided in *Biochim Biophys Acta.*, May 2010; 1804(5): 1151-1166 hereby incorporated by reference in its entirety. In addition, one may replace $Mg^{2+}$, $Zn^{2+}$, $Co^{2+}$, or $Mn^{2+}$ in the nucleotide pulse with other cations designed modulate nucleotide attachment. For example, if the nucleotide pulse replaces $Mg^{++}$ with other cation(s), such as $Na^+$, $K^+$, $Rb^+$, $Be^{++}$, $Ca^{++}$, or $Sr^{++}$, then the nucleotide can bind but not incorporate, thereby regulating whether the nucleotide will incorporate or not. Then a pulse of (optional) pre-wash without nucleotide or $Mg^{++}$ can be provided or then $Mg^{++}$ buffer without nucleotide can be provided.

By controlling the primer/initiator, the nucleotide substrate, or the polymerase, the incorporation of specific nucleic acids into the polymer can be regulated. Thus, these polymerases are capable of incorporating nucleotides independent of the template sequence and are therefore beneficial for creating nucleic acid sequences de novo. The combination of an error-prone polymerase and a primer sequence serves as a writing mechanism for imparting information into a nucleic acid sequence.

The eta-polymerase (Matsuda et al. (2000) Nature 404 (6781):1011-1013) is an example of a polymerase having a high mutation rate (~10%) and high tolerance for 3' mismatch in the presence of all 4 dNTPs and probably even higher if limited to one or two dNTPs. Hence, the eta-polymerase is a de novo recorder of nucleic acid information similar to terminal deoxynucleotidyl transferase (TdT) but with the advantage that the product produced by this polymerase is continuously double-stranded. Double stranded DNA has less sticky secondary structure and has a more predictable secondary structure than single stranded DNA. Furthermore, double stranded DNA serves as a good support for polymerases and/or DNA-binding-protein tethers.

According to certain aspects, a template dependent or template semi-dependent error prone polymerase can be used. According to certain embodiments, a template dependent polymerase may be used which may become error prone. According to certain embodiments, a template independent RNA polymerase can be used. Where a template dependent or template semi-dependent polymerase is used, any combination of templates with universal bases can be used which encourage acceptance of many nucleotide types. In addition, error tolerant cations such as $Mn^+$ can be used. Further, the present disclosure contemplates the use of error-tolerant polymerase mutants. See Berger et al., Universal Bases for Hybridization, Replication and Chain Termination, Nucleic Acids Research 2000, August 1, 28(15) pp. 2911-2914 hereby incorporated by reference. Methods of activating or inactivating template independent polymerases known to those of skill in the art are useful in the present disclosure.

Buffers

The following buffer formula is provided for TdT polymerization reactions. Other buffer formulations are known to those of skill in the art.
10 to 20 mM Tris-Acetate
20 to 50 mM Potassium Acetate
5 to 8 mM Magnesium Acetate
0.5-1.0 mM DTT
pH 7.9 in 25° C.

An exemplary buffer is provided as follows.
14 mM Tris-Acetate
35 mM Potassium Acetate
7 mM Magnesium Acetate
0.7 mM DTT
pH 7.9 in 25° C.

Acid Generating Reagents

The present disclosure provides for the use of an aqueous electrolyte media such as in commonly used with electrochemical cells. The aqueous electrolyte media may further include a weakly acidic moiety participating in oxidation or reduction reaction at an electrode and releasing one or more protons or absorbing one or more hydroxide ions upon oxidation, thereby altering pH. The aqueous electrolyte media may further include one or more or a plurality of acid generating reagents. An exemplary acid-generating reagent is hydroquinone, catechol, resorcinol, Alkannin, hexahydroxynaphthoquinone, Juglone, Lapachol, Lawsone, Menatetrenone, spinochrome D, Phylloquinone, Plumbagin, spinochrome B, Menadione, 1,4-Naphthoquinone, 1,2-Naphthoquinone, 1,6-Naphthoquinone, anthraquinones, Isoindole-4,7-diones, other natural and synthetic derivatives of quinone, other phenol derivatives, pyrrole and related derivatives and polymers thereof, thiophenes and related derivatives and polymers thereof, aniline and related derivatives and polymers thereof, acetylene derivatives and polymers thereof, Bipyridiniumor and derivatives thereof and related compounds, aldehydes and alcohols, bromine oxides, cyanides, carbonates, hypochlorous acids, hypoiodous acids, thiols, organic halides, or other weakly acidic organic and inorganic compounds.

Base Generating Reagents

The present disclosure provides for the use of an aqueous electrolyte media such as in commonly used with electrochemical cells. The aqueous electrolyte media may further include a weakly basic moiety participating in an oxidation or reduction reaction at an electrode and releasing one or more hydroxide ions or absorbing one or more protons upon reduction, thereby altering pH. An exemplary base-generating reagent is 1,4-benzoquinone, 1,2-benzoquinone, 1,3-benzoquinone, anthraquinone, Duroquinone, Tetrahydroxy-1,4-benzoquinone, Alkannin, hexahydroxynaphthoquinone, Juglone, Lapachol, Lawsone, Menatetrenone, spinochrome D, Phylloquinone, Plumbagin, spinochrome B, Menadione, 1,4-Naphthoquinone, 1,2-Naphthoquinone, 1,6-Naphthoquinone, anthraquinones, Isoindole-4,7-diones, other natural and synthetic quinone derivatives, other phenol derivatives, pyrrole and related derivatives and polymers thereof, thiophenes and related derivatives and polymers thereof, aniline and related derivatives and polymers thereof, acetylene derivatives and polymers thereof, Bipyridiniumor and derivatives thereof and related compound, aldehydes, ketones, and alcohols, bromine oxides, cyanides, carbonates, hypochlorous acids, hypoiodous acids, thiols, organic halides, or other weakly basic organic or inorganic compounds.

Nucleic Acids

In general, the terms "nucleic acid molecule," "nucleic acid sequence," "nucleic acid fragment," "oligonucleotide" and "polynucleotide" are used interchangeably and are intended to include, but not limited to, a polymeric form of nucleotides that may have various lengths, either deoxyribonucleotides (DNA) or ribonucleotides (RNA), or analogs thereof. An oligonucleotide is typically composed of a specific sequence of four nucleotide bases: adenine (A); cytosine (C); guanine (G); and thymine (T) (uracil (U) for thymine (T) when the polynucleotide is RNA). The term "oligonucleotide sequence" is the alphabetical representation of a polynucleotide molecule; alternatively, the term may be applied to the polynucleotide molecule itself. This alphabetical representation can be input into databases in a computer having a central processing unit and used for bioinformatics applications such as functional genomics and homology searching. Oligonucleotides may optionally include one or more non-standard nucleotide(s), nucleotide analog(s) and/or modified nucleotides. The present disclosure contemplates any deoxyribonucleotide or ribonucleotide and chemical variants thereof, such as methylated, hydroxymethylated or glycosylated forms of the bases, and the like. According to certain aspects, natural nucleotides, non-natural nucleotides, synthetic nucleotides, chain terminating nucleotides, nucleotides analogues and the like are used in the methods of making the nucleic acids described herein.

Nucleotides

The present disclosure provides for the use of natural nucleotides, non-natural nucleotides, synthetic nucleotides, chain terminating nucleotides, nucleotides analogues and the like in the methods described herein. According to certain aspects, deoxynucleotide triphosphates (dNTPs, such as dATP, dCTP, dGTP, dTTP, dUTP) may be used. According to certain aspects, ribonucleotide triphosphates (rNTPs) may be used. According to certain aspects, ribonucleotide diphosphates (rNDPs) may be used.

Examples of modified nucleotides used in the methods described herein include, but are not limited to diaminopurine, S2T, 5-fluorouracil, 5-bromouracil, 5-chlorouracil, 5-iodouracil, hypoxanthine, xantine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-D46-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, 2,6-diaminopurine and the like. Nucleic acid molecules may also be modified at the base moiety (e.g., at one or more atoms that typically are available to form a hydrogen bond with a complementary nucleotide and/or at one or more atoms that are not typically capable of forming a hydrogen bond with a complementary nucleotide), sugar moiety or phosphate backbone. Nucleic acid molecules may also contain amine-modified groups, such as aminoallyl-dUTP (aa-dUTP) and aminohexylacrylamide-dCTP (aha-dCTP) to allow covalent attachment of amine reactive moieties, such as N-hydroxy succinimide esters (NHS).

Alternatives to standard DNA base pairs or RNA base pairs in the oligonucleotides of the present disclosure can provide higher density in bits per cubic mm, higher safety (resistant to accidental or purposeful synthesis of natural toxins), easier discrimination in photo-programmed polymerases, or lower secondary structure. Such alternative base pairs compatible with natural and mutant polymerases for de novo and/or amplification synthesis are described in Betz K, Malyshev D A, Lavergne T, Welte W, Diederichs K, Dwyer T J, Ordoukhanian P, Romesberg F E, Marx A (2012) KlenTaq polymerase replicates unnatural base pairs by inducing a Watson-Crick geometry, Nature Chem. Biol. 8:612-614; See Y J, Malyshev D A, Lavergne T, Ordoukhanian P, Romesberg F E. J Am Chem Soc. 2011 Dec. 14; 133(49):19878-88, Site-specific labeling of DNA and RNA using an efficiently replicated and transcribed class of unnatural base pairs; Switzer C Y, Moroney S E, Benner S A. (1993) Biochemistry. 32(39):10489-96. Enzymatic recognition of the base pair between isocytidine and isoguanosine; Yamashige R, Kimoto M, Takezawa Y, Sato A, Mitsui T, Yokoyama S, Hirao I. Nucleic Acids Res. 2012 March; 40(6):2793-806. Highly specific unnatural base pair systems as a third base pair for PCR amplification; and Yang Z, Chen F, Alvarado J B, Benner S A. J Am Chem Soc. 2011 Sep. 28; 133(38):15105-12, Amplification, mutation, and sequencing of a six-letter synthetic genetic system. Other non-standard nucleotides may be used such as described in Malyshev, D. A., et al., Nature, vol. 509, pp. 385-388 (15 May 2014) hereby incorporated by reference in its entirety.

Nucleotide analogues may be used as substrates for enzymatic synthesis using TdT. In the general scheme of the presently disclosed methods, the distribution of extension length by TdT is important to ensure efficient and reliable encoding of information into DNA. It has been found that the extension efficiency, rate, and extension length distribution of each of the four natural nucleotides (A, C, G, and T) was different. In fact, it has been observed that dCTP shows the most optimal behavior while dATP and dGTP show the poorest behavior with respect to TdT-based DNA synthesis. Given these observations, several nucleotide analogues were screened to search for nucleotide analogues with a superior performance compared to their natural counterparts in TdT-based DNA synthesis and are provided below in Table 1.

TABLE 1

Screened nucleotide analogues.

| dATP analogues | dTTP analogues | dGTP analogues |
|---|---|---|
| 1-Borano-dATP | dUTP | d7-Deaza-dGTP |
| Alpha-Thiol-dATP | Aminoallyl-dUTP | 1-Borano-dGTP |
| 2-Amino-dATP | 5-Br-dUTP | Alpha-Thiol-dGTP |
| N6-Methyl-dATP | 5-Fluoro-dUTP | |
| 7-Deaza-dATP | 5-Iodo-dUTP | |
| 8-Chloro-dATP | 5-HydroxyM-dUTP | |
| 8-Oxo-dATP | 5-Aminoallyl-dUTP | |
| | 5-Propynyl-dUTP | |
| | 5-Propargylamino-dUTP | |
| | 5-Bromo-dUTP | |

It has been found that the following nucleotide analogues shown in FIG. 1 displayed equally good or superior efficiency, rate, and/or length distribution compared to their natural counterparts with TdT.

TABLE 2

Improved dATP alternatives.

7-Deaza-7-bromo-dATP
1-Borano-dATP (2'-Deoxyadenosine-5'-O-(1-Boranotriphosphate))
2-Amino-dATP (Diaminopurine)
7-Deaza-dATP
7-Deaza-7-iodo-dATP
Alpha-Thiol-dATP (2'-Deoxyadenosine-5'-O-(1-Thiotriphosphate))
Beta-Thiol-dATP (2'-Deoxyadenosine-5'-O-(2-Thiotriphosphate))

TABLE 3

Improved dTTP alternatives.

5-propynyl-dUTP
5-Bromo-dUTP
5-Iodo-dUTP
5-Aminoallyl-dUTP
5-Propargylamino-dUTP
Alpha-Thiol-dTTP (2'-Deoxythymidine-5'-O-(1-Thiotriphosphate)
Beta-Thiol-dTTP (2'-Deoxythymidine-5'-O-(2-Thiotriphosphate)

TABLE 4

Improved dGTP alternatives.

Alpha-Thiol-dGTP (2'-Deoxyguanidine-5'-O-(1-Thiotriphosphate)
Beta-Thiol-dGTP (2'-Deoxyguanidine-5'-O-(2-Thiotriphosphate)

In general, it has been observed that all nucleotide analogues that are more positively charged than their natural counterparts are far more efficient substrates of TdT. These analogues include, but are not limited to, 5-Aminoallyl-dUTP and 5-Propargylamino-dUTP.

Additional nucleotide analogues within the scope of the present disclosure include

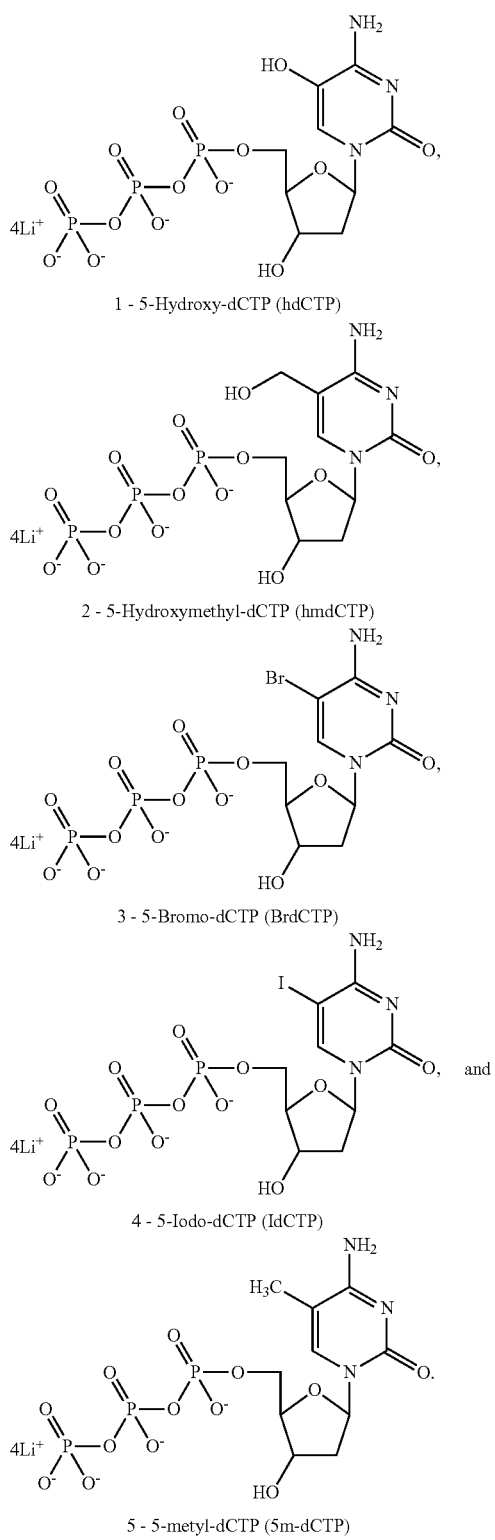

1 - 5-Hydroxy-dCTP (hdCTP)

2 - 5-Hydroxymethyl-dCTP (hmdCTP)

3 - 5-Bromo-dCTP (BrdCTP)

4 - 5-Iodo-dCTP (IdCTP) and

5 - 5-metyl-dCTP (5m-dCTP)

Supports and Attachment

The disclosure provides that one or more oligonucleotide sequences described herein, such as primers, initiators, nucleic acids, oligonucleotides or polynucleotides are immobilized on a support (e.g., a solid and/or semi-solid support). In certain aspects, an oligonucleotide sequence can be attached to a support using one or more of a phosphoramidite linker known to those of skill in the art. Suitable supports include, but are not limited to, slides, beads, chips, particles, strands, gels, sheets, tubing, spheres, containers, capillaries, pads, slices, films, plates and the like. In various embodiments, a solid support may be biological, nonbiological, organic, inorganic, or any combination thereof. Supports of the present invention can be any shape, size, or geometry as desired. For example, the support may be square, rectangular, round, flat, planar, circular, tubular, spherical, and the like. When using a support that is substantially planar, the support may be physically separated into regions, for example, with trenches, grooves, wells, or chemical barriers (e.g., hydrophobic coatings, etc.). Supports may be made from glass (silicon dioxide), metal, ceramic, polymer or other materials known to those of skill in the art. Supports may be a solid, semi-solid, elastomer or gel. In certain exemplary embodiments, a support is an array or a microarray. As used herein, the term "array" or "microarray" refers in one embodiment to a type of array that comprises a solid phase support having a substantially planar surface on which there is an array of spatially defined non-overlapping regions or sites that each contain an immobilized hybridization probe. "Substantially planar" means that features or objects of interest, such as probe sites, on a surface may occupy a volume that extends above or below a surface and whose dimensions are small relative to the dimensions of the surface. For example, beads disposed on the face of a fiber optic bundle create a substantially planar surface of probe sites, or oligonucleotides disposed or synthesized on a porous planar substrate create a substantially planar surface. Spatially defined sites may additionally be "addressable" in that its location and the identity of the immobilized probe at that location are known or determinable.

The solid supports can also include a semi-solid support such as a compressible matrix with both a solid and a liquid component, wherein the liquid occupies pores, spaces or other interstices between the solid matrix elements. Preferably, the semi-solid support materials include polyacrylamide, cellulose, poly dimethyl siloxane, polyamide (nylon) and cross-linked agarose, -dextran and -polyethylene glycol. Solid supports and semi-solid supports can be used together or independent of each other.

Supports can also include immobilizing media. Such immobilizing media that are of use according to the invention are physically stable and chemically inert under the conditions required for nucleic acid molecule deposition and amplification. A useful support matrix withstands the rapid changes in, and extremes of, temperature required for PCR. The support material permits enzymatic nucleic acid synthesis. If it is unknown whether a given substance will do so, it is tested empirically prior to any attempt at production of a set of arrays according to the invention. According to one embodiment of the present invention, the support structure comprises a semi-solid (i.e., gelatinous) lattice or matrix, wherein the interstices or pores between lattice or matrix elements are filled with an aqueous or other liquid medium; typical pore (or 'sieve') sizes are in the range of 100 µm to 5 nm. Larger spaces between matrix elements are within tolerance limits, but the potential for diffusion of amplified products prior to their immobilization is increased. The semi-solid support is compressible. Lastly, a support material of use according to the invention permits immobilizing (covalent linking) of nucleic acid features of an array to it by means known to those skilled in the art. Materials that satisfy these requirements comprise both organic and inorganic substances, and include, but are not limited to, polyacrylamide, cellulose and polyamide (nylon), as well as cross-linked agarose, dextran or polyethylene glycol.

Oligonucleotides immobilized on microarrays include nucleic acids that are generated in or from an assay reaction. Typically, primers, initiators, oligonucleotides or polynucleotides attached to a substrate are single stranded and are covalently attached to the solid phase support, usually by a 5'-end or a 3'-end. In certain exemplary embodiments, primers, initiators, oligonucleotides or polynucleotides are immobilized via one or more cleavable linkers. The density of non-overlapping regions containing nucleic acids in a microarray is typically greater than 100 per cm$^2$, and more typically, greater than 1000 per cm$^2$. Microarray technology relating to nucleic acid probes is reviewed in the following exemplary references: Schena, Editor, Microarrays: A Practical Approach (IRL Press, Oxford, 2000); Southern, Current Opin. Chem. Biol., 2: 404-410 (1998); Nature Genetics Supplement, 21:1-60 (1999); and Fodor et al, U.S. Pat. Nos. 5,424,186; 5,445,934; and 5,744,305.

Methods of immobilizing oligonucleotides to a support are known in the art (beads: Dressman et al. (2003) Proc. Natl. Acad. Sci. USA 100:8817, Brenner et al. (2000) Nat. Biotech. 18:630, Albretsen et al. (1990) Anal. Biochem. 189:40, and Lang et al. Nucleic Acids Res. (1988) 16:10861; nitrocellulose: Ranki et al. (1983) Gene 21:77; cellulose: Goldkorn (1986) Nucleic Acids Res. 14:9171; polystyrene: Ruth et al. (1987) Conference of Therapeutic and Diagnostic Applications of Synthetic Nucleic Acids, Cambridge U.K.; teflon-acrylamide: Duncan et al. (1988) Anal. Biochem. 169:104; polypropylene: Polsky-Cynkin et al. (1985) Clin. Chem. 31:1438; nylon: Van Ness et al. (1991) Nucleic Acids Res. 19:3345; agarose: Polsky-Cynkin et al., Clin. Chem. (1985) 31:1438; and sephacryl: Langdale et al. (1985) Gene 36:201; latex: Wolf et al. (1987) Nucleic Acids Res. 15:2911). Supports may be coated with attachment chemistry or polymers, such as amino-silane, NHS-esters, click chemistry, polylysine, etc., to bind a nucleic acid to the support.

As used herein, the term "attach" refers to both covalent interactions and noncovalent interactions. A covalent interaction is a chemical linkage between two atoms or radicals formed by the sharing of a pair of electrons (i.e., a single bond), two pairs of electrons (i.e., a double bond) or three pairs of electrons (i.e., a triple bond). Covalent interactions are also known in the art as electron pair interactions or electron pair bonds. Noncovalent interactions include, but are not limited to, van der Waals interactions, hydrogen bonds, weak chemical bonds (i.e., via short-range noncovalent forces), hydrophobic interactions, ionic bonds and the like. A review of noncovalent interactions can be found in Alberts et al., in Molecular Biology of the Cell, 3d edition, Garland Publishing, 1994. According to certain aspects, affixing or immobilizing nucleic acid molecules to the substrate is performed using a covalent linker that is selected from the group that includes oxidized 3-methyl uridine, an acrylyl group and hexaethylene glycol.

Nucleic acids that have been synthesized on the surface of a support may be removed, such as by a cleavable linker or linkers known to those of skill in the art. Linkers can be designed with chemically reactive segments which are optionally cleavable with agents such as enzymes, light, heat, pH buffers, and redox reagents. Such linkers can be employed to pre-fabricate an in situ solid-phase inactive reservoir of a different solution-phase primer for each discrete feature. Upon linker cleavage, the primer would be released into solution for PCR, perhaps by using the heat from the thermocycling process as the trigger. It is also contemplated that affixing of nucleic acid molecules to the support is performed via hybridization of the members of the pool to nucleic acid molecules that are covalently bound to the support.

Supports described herein may have one or more electrodes positioned at or near or adjacent to a reaction site such that oxidation or reduction may take place within a reaction zone including the reaction site.

Reagent Delivery Systems

The disclosure provides that one or more or a plurality of reagents and washes are delivered to one or more or a plurality of reaction sites within one or more or a plurality of reaction zones including an electrode or electrodes in a method of covalently attaching dNTP to an initiator sequence or an existing nucleotide attached at the desired location using electricity to alter pH within a reaction zone. A selected nucleotide reagent liquid is pulsed or flowed or deposited at the reaction site where reaction takes place and then may be optionally followed by delivery of a buffer or wash that does not include the nucleotide. Suitable delivery systems include fluidics systems, microfluidics systems, syringe systems, ink jet systems, pipette systems and other fluid delivery systems known to those of skill in the art. Various flow cell embodiments or flow channel embodiments or microfluidic channel embodiments are envisioned which can deliver separate reagents or a mixture of reagents or washes using pumps or electrodes or other methods known to those of skill in the art of moving fluids through channels or microfluidic channels through one or more channels to a reaction region or vessel where the surface of the substrate is positioned so that the reagents can contact the desired location where a nucleotide is to be added.

The disclosure provides that a microfluidic device is provided with one or more reservoirs which include one or more reagents which are then transferred via microchannels to a reaction zone where the reagents are mixed and the reaction occurs. Such microfluidic devices and the methods of moving fluid reagents through such microfluidic devices are known to those of skill in the art.

Reagents can be deposited onto a discrete region of the support, such that each region forms a feature of the array. The pH of the feature is capable of being altered, i.e. the pH is raised or lowered to either activate or deactivate an enzyme that catalyzes addition of a dNTP as described herein.

The following examples are set forth as being representative of the present disclosure. These examples are not to be construed as limiting the scope of the present disclosure as these and other equivalent embodiments will be apparent in view of the present disclosure, figures and accompanying claims.

Example I

Modulating TdT Enzymatic Activity by pH

Application of current through an electrolyte results in oxidative generation of acids at the anode and reductive generation of bases at the cathode. Applying current to water directly results in such reactions referred to as hydrolysis. In water electrolysis, the following reactions take place at the electrodes:

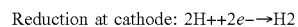

Reduction at cathode: $2H^+ + 2e^- \rightarrow H_2$

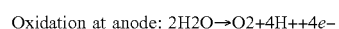

Oxidation at anode: $2H_2O \rightarrow O_2 + 4H^+ + 4e^-$

The disclosure provides that production of acid at the anode can further be enhanced and facilitated by adding easily-oxidized moieties to the electrolyte. For example, Hydroquinone (benzene-1,4-diol) and some of its derivatives can be easily oxidized and their inclusion in the electrolyte enhances and facilitates the generation of acids at the anode:

Hydroquionone (HQ) oxidation at anode: HQ→Q+ 2H++2e−

The disclosure provides for the use of one or more or a plurality of different reagents in an electrolyte to facilitate acid generation at the anode based on the pH, the amount of current desired or required for the oxidation reaction, electrolyte composition, etc. Hydroquinone is one example of a moiety that enhances acid production in the electrolyte, but water alone can generate acids or it can be combined with numerous other compounds. Generation of acid using an electrical current is described in U.S. Pat. No. 6,280,595, Egeland R D, Southern E M. Electrochemically directed synthesis of oligonucleotides for DNA microarray fabrication. Nucleic Acids Res. [Internet] 2005; 33(14):e125; Maurer K, Cooper J, Caraballo M, Crye J, Suciu D, Ghindilis A, et al. Electrochemically generated acid and its containment to 100 micron reaction areas for the production of DNA microarrays. PLoS One [Internet]. 2006; 1(1):e34 and Gao X, LeProust E, Zhang H, Srivannavit O, Gulari E, Yu P, et al. A flexible light-directed DNA chip synthesis gated by deprotection using solution photogenerated acids. Nucleic Acids Res [Internet]. 2001 Nov. 15; 29(22):4744-50, each of which are hereby incorporated by reference in its entirety.

The range of pH in which TdT is active was determined.

1. A buffer of 50 mM Tris (base) and 50 mM Boric acid was prepared and its pH (initially at ~8.5) was adjusted to 6.05, 6.9, 7.93, 8.96, 10.02, and 11.07 using acetic acid and sodium hydroxide. These buffers serve as 2× buffers in the experiments.

2. Extension reactions were assembled as follows:
Water: 5 µl
2× Buffer: 10 µl
25 µM initiator: 1 µl
100 mM MgSO$_4$ or water: 2 µl
1 mM dCTP: 1 µl
TdT (20 U/µl): 1 µl
Total Volume: 20 µl 3. Each reaction was incubated for 15 minutes and then loaded on a TBE-Urea gel with an unextended initiator for comparison.

Figure 2:
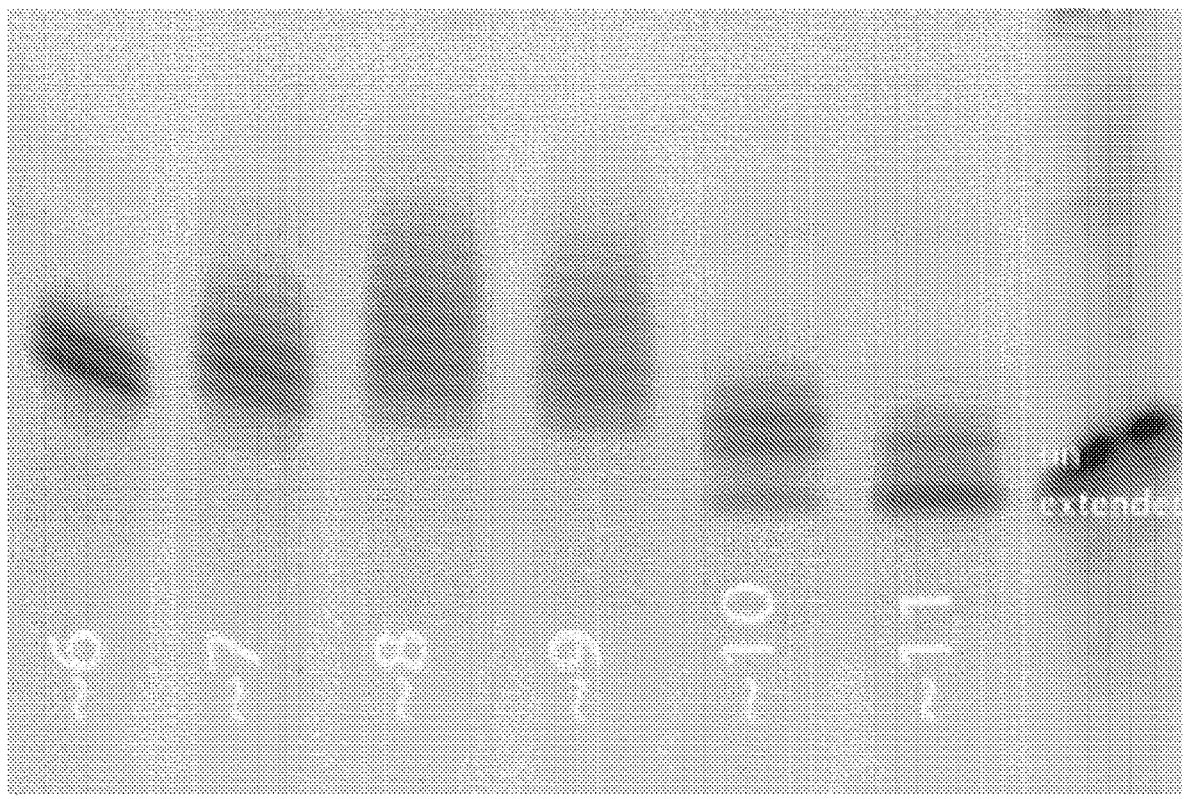
FIG. 2 depicts results for pH regulation of TdT enzyme activity on a TBE-Urea gel.

As shown in FIG. 2, the results in the TBE-Urea gel established that pH can be used to regulate the activity of TdT enzyme in a way that is adaptable for pH-based TdT-control for data storage. It also needs to be established that the effects of pH on TdT are reversible; that is, the enzyme's activity can be substantially reduced at an unfavorable pH but can be reverted back to normal activity at favorable pH. The ensuing experiment was performed to evaluate this question.

In the following experiment, TdT was incubated at a pH for 15 minutes without the nucleotide or the initiator, it was then combined with the nucleotide and the initiator in such a way that the final pH of the mixture during polymerization would be different from that of the initial 15 min incubation.

1. A buffer of 50 mM Tris (base) and 50 mM Boric acid was prepared and its pH (initially at ~8.5) was adjusted to 6.05, 6.9, 7.93, 8.96, 10.02, and 11.07 using acetic acid and sodium hydroxide. These buffers serve as 2× buffers in the experiment.

2. Extension reactions were assembled in two parts:
Part 1:
Water: 5 µl
2× Buffer: 5 µl
100 mM MgAc: 2 µl
TdT (20 U/µl): 1 µl
Total Volume: 10 µl
Part 2:
Water: 3 µl
2× Buffer: 5 µl
25 µM initiator: 1 µl
1 mM dCTP: 1 µl
Total Volume: 10 µl Eight different extension reactions were assembled with following pH used for the buffer in part1 and part2:

| Reaction | A | B | C | D | E* | F | G | H | I |
|---|---|---|---|---|---|---|---|---|---|
| Part 1 Buffer | 6 | 6 | 6 | 8 | 6 + 11 | 9 | 11 | 11 | 11 |
| Part 2 Buffer | 6 | 10 | 11 | 8 | 6 + 11 | 9 | 6 | 7 | 11 |

Figure 3:
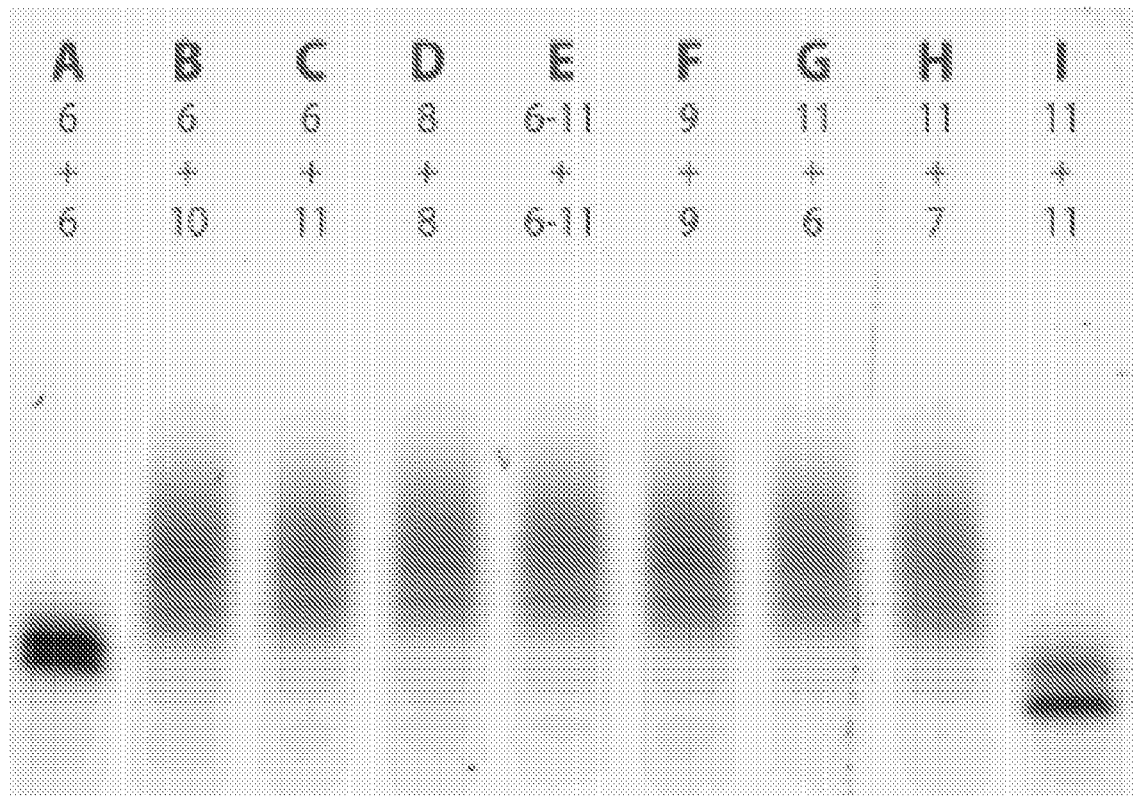
FIG. 3 depicts results for reversible pH regulation of TdT enzyme activity on a TBE-Urea gel. Top value for each lane indicates the pH that TdT was incubated at before the start of the polymerization reaction. Bottom value for each lane indicates the adjusted pH during the polymerization reaction.

3. Both parts of each reaction were incubated for 15 minutes, they were then mixed to form the 20 µl total, then loaded on a TBE-Urea gel:

As shown in FIG. 3, TdT is highly active in pH ranges that are above 6 and below 11, and it is substantially inactivated at pH ranges that are below 6 and above 11. It was clear from this experiment that the enzymatic activity of TdT could be reversibly inhibited by both increasing and reducing the pH. Inhibition of TdT enzymatic activity was more effective at pH~11 than it was at pH~6.

For example, as shown in FIG. 3 in lanes A and I, the starting pH was 6 and 11 respectively where the enzyme showed little to no polymerization activity. Lanes B and C showed that when the enzyme was kept at pH=6 it could be activated by increasing the pH to more alkaline values. Lanes G and H showed that when the enzyme was kept at pH=11, it could be activated by decreasing the pH to more acidic values. Since the enzyme apparently did not denature irreversibly at either pH=6 or pH=11, it was clear that the effect of pH on the enzymatic activity was reversible and the enzyme could be activated and inactivated multiple times by changing the pH. Therefore, it has been demonstrated that TdT could be reversibly inactivated by changing the pH of the reaction solution to 11 or above. Specifically, the enzyme was highly active in pH from 6 to 10 and largely inactive at pH greater than 11 but could be reactivated once the pH is lowered back within 6-10 range.

Example II

Assembly of an Electrochemical Cell for Use with Enzymatic Nucleic Acid Synthesis The present disclosure provides for a method of controlling activity of an enzyme, such as TdT, using electrical current by converting the current to a change in pH in the environment around TdT, thereby conferring electrical control over the activity of TdT. The disclosure provides for the production of acid at an anode to control DNA synthesis using TdT in an aqueous solution. Altering pH from an inactivating pH to an activating pH provides electrical control over TdT activity which allows for high throughput and highly parallelized synthesis of DNA and control over the information content of the DNA.

An electrochemical cell was constructed as follows.

A 5Am-f3-primer (5NH3-TTTTUCTACACTCTTTC-CCTACACGACGCTCTTC) (SEQ ID NO:1) was immobilized on an aldehyde-coated microarray slide in spots of roughly 0.2 mm in diameter according to standard microarray protocols as suggested by the manufacturer (Schott).

Figure 4:
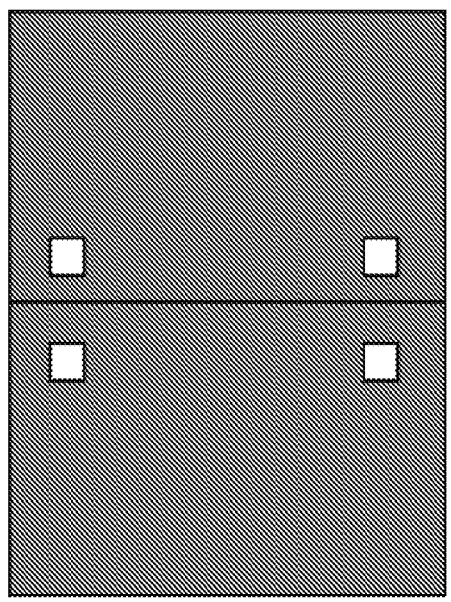
FIG. 4 is a schematic of a pattern etched in an indium tin oxide coating on a polyethylene film used in the manufacture of an electrochemical cell for use in the methods described herein.

An indium tin oxide (ITO) coated polyethylene film (PET, Sigma 639303) was designed as depicted in schematic in FIG. 4. A pattern was etched on the ITO coated PET including a middle line to destroy the conductivity between the top half and the lower half but not completely cut. Square holes are created for injection of the electrolyte solution containing the enzyme and other reagents. The white holes indicate the patterns that were cut out of the PET. The short dimension of the device is 20 mm.

Figure 5:
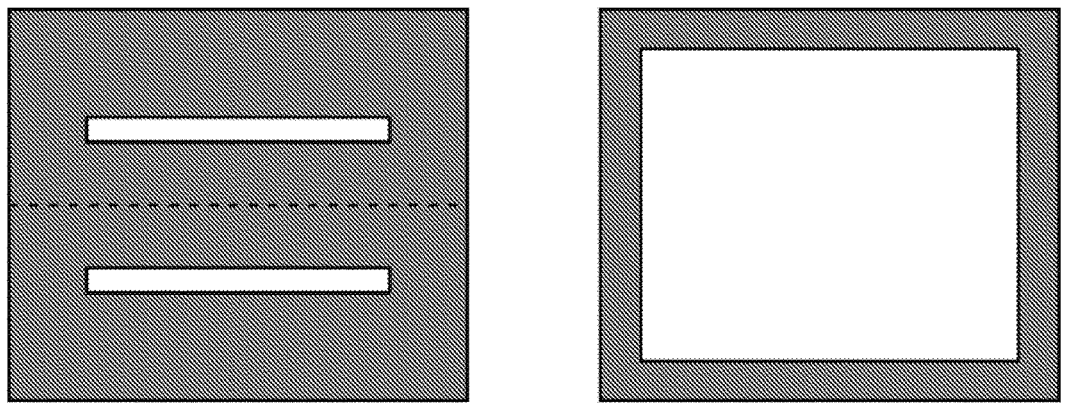
FIG. 5 is a schematic of double sided adhesive frames used in the manufacture of an electrochemical cell for use in the methods described herein.

As depicted in schematic in FIG. 5, two different frames were laser cut on 3M double-sided tape. The shapes of the double-sided adhesive frames were used to assemble the electrochemical cell. The frame on the left was placed on the conductive side of the ITO-coated PET with the dashed line aligning with the middle line of the ITO-coated PET in FIG. 4, creating two separated conductive surfaces or electrodes on the PET with other areas being covered by the adhesive. The frame on the right was placed on the glass slide with initiators immobilized onto its surface so that the immobilized DNA patches of interest, i.e. the initiators, were surrounded by the frame. The white parts indicate the patterns cut out of the double-sided adhesive. Each adhesive layer is 100 microns thick. The long dimension of each device is 20 mm.

Figure 6:
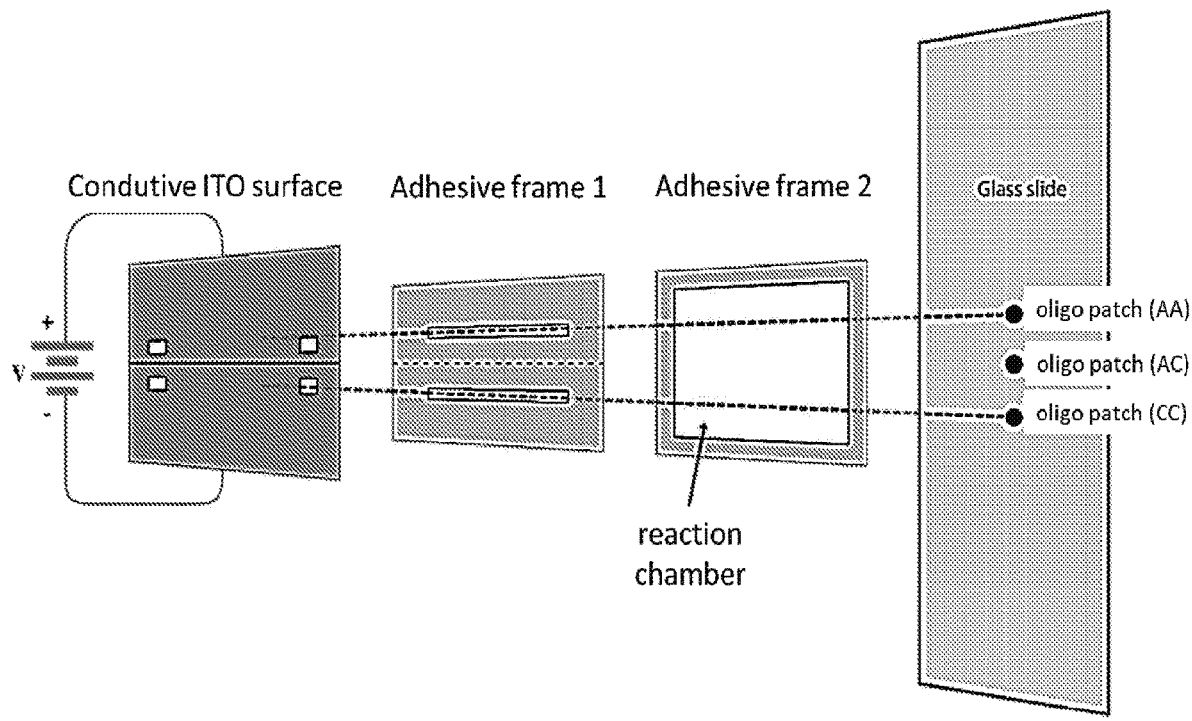
FIG. 6 is a schematic of an assembly of an electrochemical cell for use in the methods described herein.

As depicted in FIG. 6 in schematic, the adhesive covered PET and DNA-containing glass slides were then adhered to each other so as to align the outer frames of the adhesives while placing certain DNA patches, i.e. the initiators, exactly opposite the electrodes, i.e. the anode (AA) and the cathode (CC) or in between (AC) as indicated by the dashed lines, on the ITO-coated PET surface. Each adhesive layer is 100 microns thick. This assembly is the complete electrochemical cell.

Example III

Use of Electrochemical Cell for Enzymatic Nucleic Acid Synthesis

Figure 7:
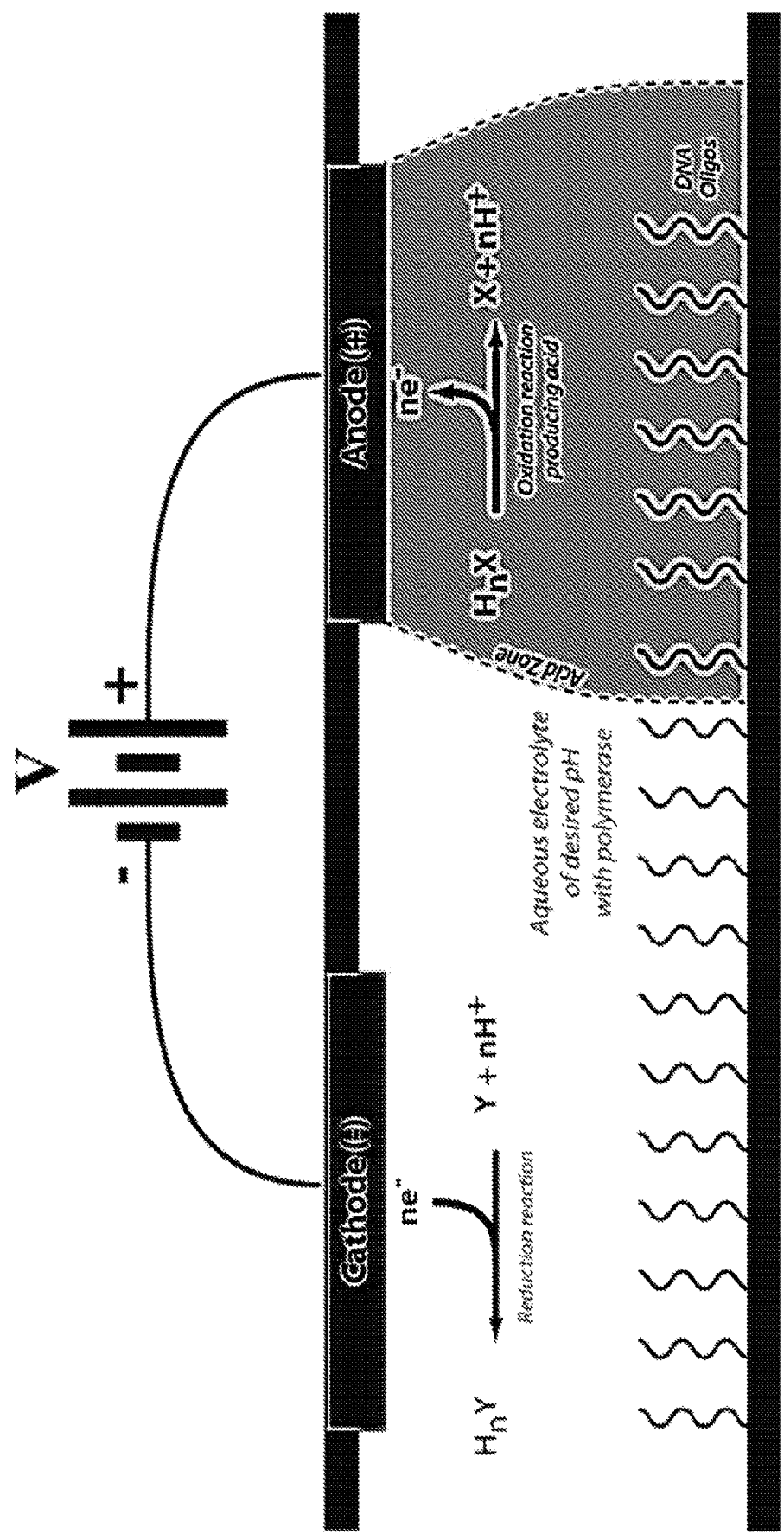
FIG. 7 is a schematic of an electrochemical cell with an anode and cathode positioned adjacent to a substrate including initiators attached thereto. An aqueous electrolyte is in contact with the anode and the cathode and the substrate including initiators attached thereto. Application of a voltage to the electrochemical cell results in an oxidation reaction at the anode creating a reaction zone including a reaction site including a portion of the substrate with the initiators attached thereto. The schematic is for exemplary purposes only to show that an oxidation reaction generates an acid which lowers pH in a reaction zone which activates enzymatic nucleotide addition at a reaction site within the reaction zone. The enzyme can then be inactivated by diffusive dispersion of the acid or by reversal of the current and generation of base at the reaction zone.

An electrochemical cell was assembled as described in Example II and as shown in schematic in FIG. 7. With reference to FIG. 7, initiator DNA oligonucleotides were immobilized at a short distance (about 100 microns) from an electrode array. The cell is filled with an electrolyte at an inactivating pH together with TdT and a dNTP. X is an electron donor such as aqueous oxygen or Hydroquinone. Y is an electron acceptor, such as Benzoquinone, Anthraquinone, aqueous oxygen, which can be the same as X or be different. The electrolyte solution is buffered at a pH in which a polymerase, such as TdT, is inactive, such as pH=11. A desired dNTP or a mixture of dNTPs is present in this solution. Upon applying current to the system, acid is generated at the anode creating a reaction zone or Acid Zone, thereby activating the polymerase in that region and resulting in extension of the initiator oligonucleotides with the desired base at the reaction site. The reaction can be stopped by either stopping the current or reversing it to neutralize the acid in the reaction zone to raise the pH thereby inactivating the TdT.

For purposes of demonstrating electrical control over TdT activity in a pH-based device, two identical electrochemical cells were assembled as described in Example II and as shown in schematic in FIG. 7. One was filled with the "positive" reaction mixture below, the other with the "indicator" reaction mixture that contained a pH indicator dye, o-cresophthalein, instead of TdT. O-cresophthalein is a pH reporter that is pink above pH=9.8 and colorless below that pH.

Positive: 5 mM Piperidine, 25 mM TrisAcetate, 10 mM Magnesium Acetate, 500 uM dCTP, 1 U/ul TdT, pH adjusted to 11.

Indicator: 5 mM Piperidine, 25 mM TrisAcetate, 10 mM Magnesium Acetate, 500 uM dCTP, 250 ug/ml o-cresophthalein, pH adjusted to 11.

The reaction chambers were connected to each other in series and then to a power supply. This circuit was subjected to 100 micro Amperes of current for 1 minute. At this point, in the "indicator" cell, the solution above the anode lost its pink color showing a drop in pH. The current was turned off and the cells were incubated for 5 minutes.

The glass slide was separated from the rest of the electrochemical cell and washed. Three oligo patches from the glass slide, one that had been placed opposite the anode (AA), one that had been placed opposite the cathode (CC), and one that had been placed opposite the space between the anode and the cathode (AC) were removed from the glass slide by treatment with a solution of 5 ul of 10 U/ul Uridine Deglycosylase and 10 U/ul of Endonuclease VIII in 1×SSC.

The AA, AC, and CC samples were ligated to the 5P-r9-adaptor (5P-CAGTC AGATCGGAAGAGCACACGTCTGAACTCCAGTCA) (SEQ ID NO:2) in 20 ul total volume containing 10 U T4 RNA Ligase, 25% PEG8K, 10 uM dATP, and 1×T4 RNA Ligase Buffer (NEB) overnight at room temperature. 1 uL (from the 20 uL total) of each ligation reaction was amplified with primers corresponding to 5P-r9-adaptor and 5AM-f3-primer in a PCR reaction. The PCR product of each sample was run on a 4% Agarose gel.

Figure 8:
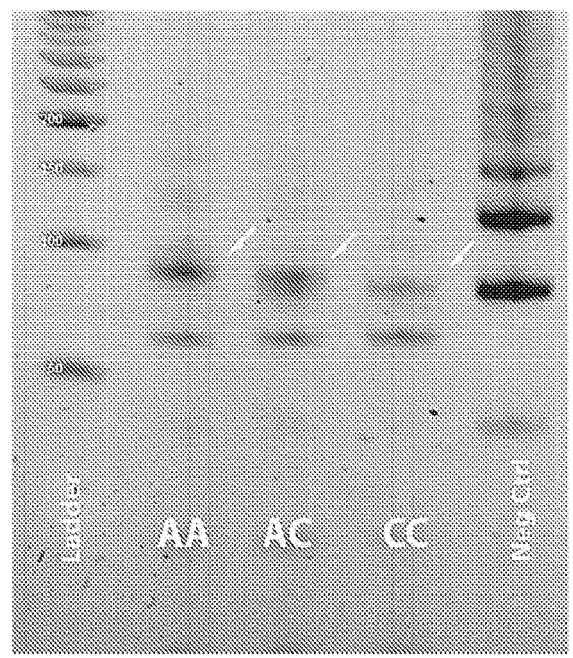
FIG. 8 is a gel image of results of DNA extension using TdT in an electrochemical cell.
Figure 9:
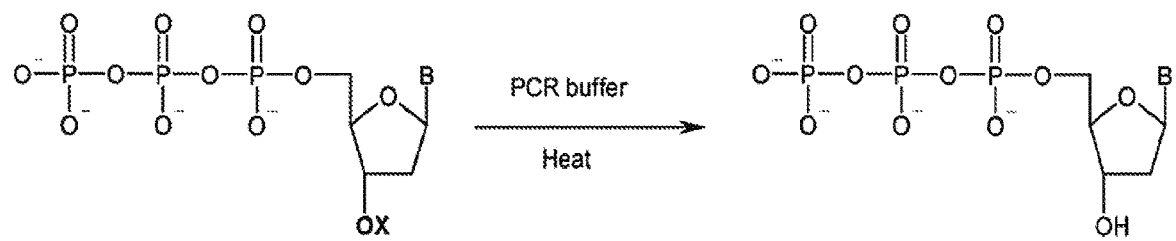
FIG. 9 depicts 3'-modified reversible terminators.
Figure 9:
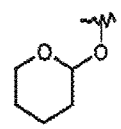
Figure 9:
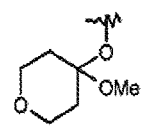
Figure 9:
Figure 9:
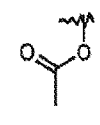
Figure 9:
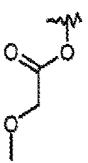
Figure 9:
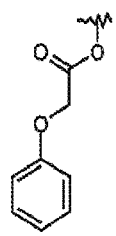
Figure 10:
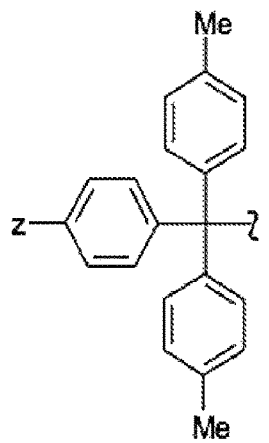
FIG. 10 depicts 3'-modified reversible terminators.
Figure 10:
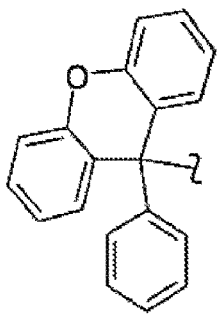
Figure 10:
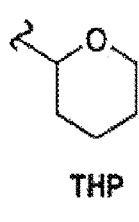
Figure 10:
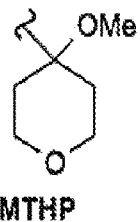
Figure 10:
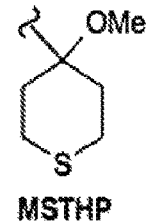
Figure 10:
Figure 10:
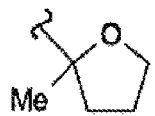
Figure 10:
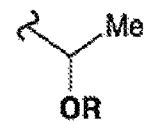
Figure 10:
Figure 10:
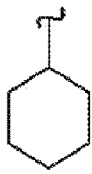
Figure 10:
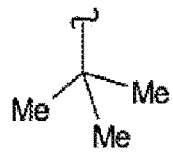
Figure 10:
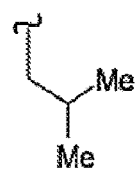
Figure 10:
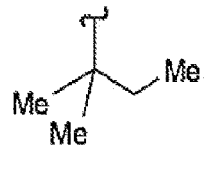
Figure 11:
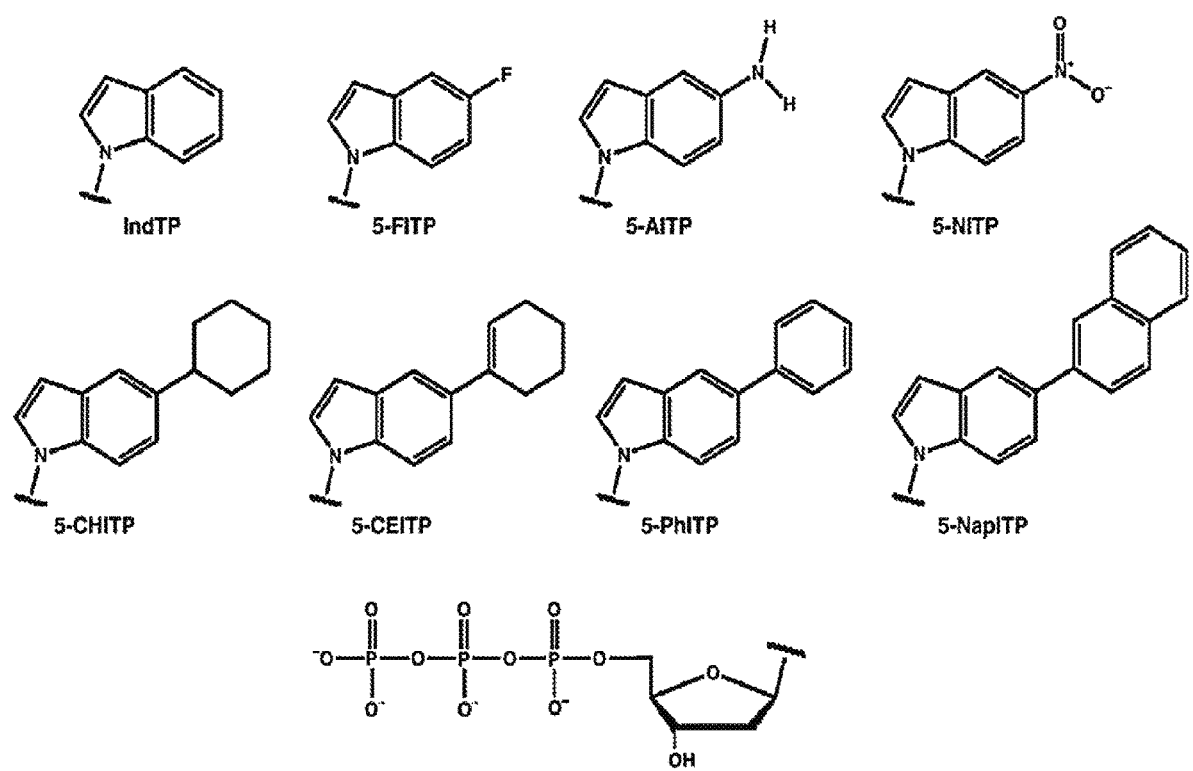
FIG. 11 depicts base-modified nucleotides.

The results of DNA extension with TdT in an electrochemical cell are shown in FIG. 8. Negative control represents the 5AM-f3-primer ligated with 5P-r9-adaptor and amplified in PCR as a non-extended control. The laddering is due to concatemerization of 5P-r9-adaptors in the ligation step. However, the smallest band of about 80 bp represents the expected product size of a monomer. Arrows point to the extension of the 5AM-f3-primer on the anode in the electrochemical cell. AA is the sample placed over the anode, CC is the sample placed over the cathode, and AC is the sample placed between the anode and the cathode.

The cathode samples (CC) are not extended since no pH drop has occurred to activate TdT to enable polymerization. In contrast, the anode samples (AA) show extension due to electrically-induced pH change enabling activation of TdT for polymerization. AC samples are of DNA initiators that were placed in the horizontal junction such that half of the initiators were in the anode and the other half of the initiators were on the cathode; these samples show two bands—one with extension and the other without. Thus, extension with TdT is localized only to the anode. This example is extended to massively parallel synthesis of DNA by electrically addressable electrodes to activate TdT via pH.

Example IV

Exemplary Embodiments

The present disclosure provides a method for making a polynucleotide including (a) combining a selected nucleotide triphosphate, one or more cations, and an error prone or template independent DNA polymerase in aqueous electrolyte media at a reaction site including an initiator sequence attached thereto and having a 3' terminal nucleotide, wherein the reaction site is at an inactivating pH that renders the error prone or template independent DNA polymerase inactive to add the selected nucleotide triphosphate to the initiator sequence, and wherein the reaction site is within a reaction zone including an electrode of an electrochemical cell wherein the electrode is an anode or a cathode of the electrochemical cell; (b) applying voltage to the electrochemical cell to generate an acid or a base in the aqueous electrolyte media at the reaction zone to alter pH in the reaction zone to create an activating pH to activate the error prone or template independent DNA polymerase, wherein reaction reagents are present at selected concentrations and under conditions which covalently add one or more of the selected nucleotide triphosphate to the 3' terminal nucleotide such that the selected nucleotide triphosphate becomes a 3' terminal nucleotide and under conditions wherein a desired number of the selected nucleotide triphosphate is added to the initiator sequence, and (c) repeating steps (a) and (b) until the polynucleotide is formed. The disclosure provides that the electrode within the reaction zone is an anode. The disclosure provides that the electrode within the reaction zone is a cathode. The disclosure provides that the reaction site is at or near or adjacent the anode of the electrochemical cell and applying a voltage between the anode and the cathode results in generation of an acid at the anode. The disclosure provides that the aqueous electrolyte media further includes an acid-generating reagent. The disclosure provides that the aqueous electrolyte media further includes a weakly acidic moiety participating in an oxidation or reduction reaction at an electrode and releasing one or more protons or absorbing one or more hydroxide ions upon oxidation. The disclosure provides that the aqueous electrolyte media further includes a weakly basic moiety participating in an oxidation or reduction reaction at an electrode and releasing one or more hydroxide ions or absorbing one or more protons upon reduction. The disclosure provides that the error prone or template independent DNA polymerase is terminal deoxynucleotide transferase and the inactivating pH is equal to or more than 11 and the activating pH is less than 11. The disclosure provides that the error prone or template independent DNA polymerase is terminal deoxynucleotide transferase and the inactivating pH is equal to or below 4 and the activating pH is greater than 4. The disclosure provides that step (b) further includes returning the reaction zone to an inactivating pH. The disclosure provides that step (b) further includes returning the reaction zone to an inactivating pH by addition of a base to the reaction zone. The disclosure provides that step (b) further includes returning the reaction zone to an inactivating pH by addition of an acid to the reaction zone. The disclosure provides that step (b) further includes returning the reaction zone to an inactivating pH by reversing polarity of the applied voltage. The disclosure provides that step (b) further includes returning the reaction zone to an inactivating pH by reversing polarity of the applied voltage and thereby switching position of the anode and the cathode. The disclosure provides that the error prone or template independent DNA polymerase is rendered active by the activating pH at a rate which allows addition of one or more nucleotides. The disclosure provides that the error prone or template independent DNA polymerase is rendered active by the activating pH at a rate which allows addition of one or more nucleotides after which either the reaction zone is returned to an inactivating pH or the nucleotide triphosphate is removed from the reaction zone. The disclosure provides that step (b) further includes removing reaction reagents from the reaction zone. The disclosure provides that step (b) further includes removing reaction reagents from the reaction zone by flowing a wash solution through the reaction zone. The disclosure provides that the reaction zone is within a fluidic channel. The disclosure provides that the reaction site is a surface area on the surface of a fluidic channel. The disclosure provides that the reaction site is within a fluidic channel. The disclosure provides that the reaction site is a structure within a fluidic channel. The disclosure provides that the reaction site is a collection of beads within a fluidic channel. The disclosure provides that the initiator includes one or more nucleotides. The disclosure provides further including the step of monitoring covalent addition of the selected nucleotide triphosphate. The disclosure provides that the error prone or template independent DNA polymerase is terminal deoxynucleotide transferase. The disclosure provides that the cations are one or more of $Zn^{+2}$, $Co^{+2}$, $Mg^{+2}$ or $Mn^{+2}$. The disclosure provides that the one or more cations is a divalent cation and the availability of the divalent cation at the reaction site is controlled by pH. The disclosure provides that the one or more cations is a divalent cation and the solubility of the divalent cation is reduced at the inactivating pH. The disclosure provides that the template independent or error-prone polymerase is terminal nucleotidyl transferase and the divalent ion is $Mg^{+2}$ and the inactivating pH renders $Mg^{+2}$ substantially insoluble. The disclosure provides that the template independent or error-prone polymerase is terminal nucleotidyl transferase and the divalent ion is $Mg^{+2}$ and the inactivating pH is equal to or more than 11 and the inactivating pH renders $Mg^{+2}$ substantially insoluble. The disclosure provides that the one or more cations is a divalent cation and the solubility of the divalent cation is increased at the activating pH. The disclosure provides that the template independent or error-prone polymerase is terminal nucleotidyl transferase and the divalent ion is $Mg^{+2}$ and the activating pH renders $Mg^{+2}$ substantially soluble. The disclosure provides that the template independent or error-prone polymerase is terminal nucleotidyl transferase and the divalent ion is $Mg^{+2}$ and the activating pH is less than 11 and the activating pH renders $Mg^{+2}$ substantially soluble. The disclosure provides that the selected nucleotide is a natural nucleotide or a nucleotide analog. The disclosure provides that the initiator is attached by a cleavable moiety. The disclosure provides releasing the polynucleotide from the reaction site after the desired sequence of nucleotides has been added to the 3' end of the polynucleotide. The disclosure provides releasing the polynucleotide from the reaction site using an enzyme, a chemical, light, heat or other suitable method or reagent. The disclosure provides releasing the polynucleotide from the reaction site, collecting the polynucleotide, amplifying the polynucleotide and sequencing the polynucleotide. The disclosure provides that one or more reaction reagents are removed from the reaction site and one or more additional reaction reagents are provided to the reaction site after each round of addition. The disclosure provides that a plurality of reaction sites wherein each reaction site is within a reaction zone including an electrode of an electrochemical cell wherein the electrode is an anode or a cathode of the electrochemical cell and wherein addition of a nucleotide triphosphate at each of the plurality of reaction sites is independently controlled by separate application of voltages. The disclosure provides that a plurality of reaction sites wherein each reaction site is within a reaction zone including an electrode of an electrochemical cell wherein the electrode is an anode or a cathode of the electrochemical cell and wherein one or more reaction reagents are provided to each of the plurality of reaction sites and a separate voltage is applied to the electrochemical cell. The disclosure provides that plurality of reaction sites and a corresponding plurality of reaction zones and electrodes of electrochemical cells wherein reaction at each of the plurality of reaction sites is independently controlled by application of separate voltages to the electrochemical cells. The disclosure provides a plurality of reaction sites and a corresponding plurality of reaction zones and electrodes of electrochemical cells wherein one or more reaction reagents are provided to each of the plurality of reaction sites and reaction at each of the plurality of reaction sites is independently controlled by application of separate voltages to the electrochemical cells.

The disclosure provides a method for making a plurality of polynucleotides including (a) combining a selected nucleotide triphosphate, cations, and an error prone or template independent DNA polymerase in aqueous electrolyte media at a plurality of reaction sites including an initiator sequence attached thereto and having a 3' terminal nucleotide, wherein each reaction site is at an inactivating pH that renders the error prone or template independent DNA polymerase inactive to add the selected nucleotide triphosphate to the initiator sequence, and wherein each reaction site is within a corresponding reaction zone including an electrode of a corresponding electrochemical cell wherein the electrode is an anode or a cathode of the electrochemical cell thereby providing a plurality of reaction zones and a plurality of corresponding electrochemical cells; (b) applying separate voltages to each of the corresponding electrochemical cells to generate an acid or a base in the aqueous electrolyte media at the corresponding reaction zone to alter pH in the corresponding reaction zone to create an activating pH to activate the error prone or template independent DNA polymerase, wherein reaction reagents are present at selected concentrations and under conditions which covalently add one or more of the selected nucleotide triphosphate to the 3' terminal nucleotide such that the selected nucleotide triphosphate becomes a 3' terminal nucleotide and under conditions wherein a desired number of the selected nucleotide triphosphate is added to the initiator sequence, and (c) repeating steps (a) and (b) until the plurality of polynucleotides is formed.

Other Embodiments

Other embodiments will be evident to those of skill in the art. It should be understood that the foregoing description is provided for clarity only and is merely exemplary. The spirit and scope of the present invention are not limited to the above examples, but are encompassed by the following claims. All publications and patent applications cited above are incorporated by reference in their entirety for all purposes to the same extent as if each individual publication or patent application were specifically and individually indicated to be so incorporated by reference.

The invention claimed is:
1. A method for making a polynucleotide comprising
(a) combining a selected nucleotide triphosphate, one or more cations, and an error prone polymerase or template independent DNA polymerase in aqueous electrolyte media at a reaction site including an initiator sequence attached thereto and having a 3' terminal nucleotide,
wherein the reaction site is at an inactivating pH that renders the error prone polymerase or template independent DNA polymerase inactive to add the selected nucleotide triphosphate to the initiator sequence, and wherein the reaction site is within a reaction zone including an electrode of an electrochemical cell wherein the electrode is an anode or a cathode of the electrochemical cell;
(b) applying voltage or current to the electrochemical cell to generate an acid or a base in the aqueous electrolyte media at the reaction zone to alter pH in the reaction zone to create an activating pH to activate the error prone polymerase or template independent DNA polymerase,
wherein reaction reagents are present at selected concentrations and under conditions which covalently add one or more of the selected nucleotide triphosphate to the 3' terminal nucleotide such that the selected nucleotide triphosphate becomes a 3' terminal nucleotide and under conditions wherein a desired number of the selected nucleotide triphosphate is added to the initiator sequence, and
(c) repeating steps (a) and (b) until the polynucleotide is formed.

2. The method of claim 1 wherein the electrode within the reaction zone is an anode.

3. The method of claim 1 wherein the electrode within the reaction zone is a cathode.

4. The method of claim 1 wherein the reaction site is at or near or adjacent the anode of the electrochemical cell and applying a voltage or current between the anode and the cathode results in generation of an acid at the anode.

5. The method of claim 1 wherein the aqueous electrolyte media further includes an acid-generating reagent.

6. The method of claim 1 wherein the aqueous electrolyte media further includes a weakly acidic moiety participating in an oxidation or reduction reaction at an electrode and releasing one or more protons or absorbing one or more hydroxide ions upon oxidation.

7. The method of claim 1 wherein the aqueous electrolyte media further includes an acid-generating reagent being a member selected from the group consisting of hydroquinone, catechol, resorcinol, Alkannin, hexahydroxynaphthoquinone, Juglone, Lapachol, Lawsone, Menatetrenone, spinochrome D, Phylloquinone, Plumbagin, spinochrome B, Menadione, 1,4-Naphthoquinone, 1,2-Naphthoquinone, 1,6-Naphthoquinone, anthraquinones, Isoindole-4,7-diones, quinone, phenol, pyrrole, thiophenes, aniline, acetylene, and Bipyridiniumor.

8. The method of claim 1 wherein the aqueous electrolyte media further includes a weakly basic moiety participating in an oxidation or reduction reaction at an electrode and releasing one or more hydroxide ions or absorbing one or more protons upon reduction.

9. The method of claim 1 wherein the aqueous electrolyte media further includes a base-generating reagent being a member selected from the group consisting of 1,4-benzoquinone, 1,2-benzoquinone, 1,3-benzoquinone, anthraquinone, Duroquinone, Tetrahydroxy-1,4-benzoquinone, Alkannin, hexahydroxynaphthoquinone, Juglone, Lapachol, Lawsone, Menatetrenone, spinochrome D, Phylloquinone, Plumbagin, spinochrome B, Menadione, 1,4-Naphthoquinone, 1,2-Naphthoquinone, 1,6-Naphthoquinone, anthraquinones, Isoindole-4,7-diones, quinone, phenol, pyrrole, thiophenes, aniline, acetylene, and Bipyridiniumor.

10. The method of claim 1 wherein the error prone polymerase or template independent DNA polymerase is terminal deoxynucleotide transferase and the inactivating pH is equal to or more than 11 and the activating pH is less than 11.

11. The method of claim 1 wherein the error prone polymerase or template independent DNA polymerase is terminal deoxynucleotide transferase and the inactivating pH is equal to or below 4 and the activating pH is greater than 4.

12. The method of claim 1 wherein step (b) further includes returning the reaction zone to an inactivating pH.

13. The method of claim 1 wherein step (b) further includes returning the reaction zone to an inactivating pH by addition of a base to the reaction zone.

14. The method of claim 1 wherein step (b) further includes returning the reaction zone to an inactivating pH by addition of an acid to the reaction zone.

15. The method of claim 1 wherein step (b) further includes returning the reaction zone to an inactivating pH by reversing polarity of the applied voltage or current.

16. The method of claim 1 wherein step (b) further includes returning the reaction zone to an inactivating pH by reversing polarity of the applied voltage or current and thereby switching position of the anode and the cathode.

17. The method of claim 1 wherein the error prone polymerase or template independent DNA polymerase is rendered active by the activating pH at a rate which allows addition of one or more nucleotides.

18. The method of claim 1 wherein the error prone polymerase or template independent DNA polymerase is rendered active by the activating pH at a rate which allows addition of one or more nucleotides after which either the reaction zone is returned to an inactivating pH or the nucleotide triphosphate is removed from the reaction zone.

19. The method of claim 1 wherein step (b) further includes removing reaction reagents from the reaction zone.

20. The method of claim 1 wherein step (b) further includes removing reaction reagents from the reaction zone by flowing a wash solution through the reaction zone.

21. The method of claim 1 wherein the reaction zone is within a fluidic channel.

22. The method of claim 1 wherein the reaction site is a surface area on the surface of a fluidic channel.

23. The method of claim 1 wherein the reaction site is within a fluidic channel.

24. The method of claim 1 wherein the reaction site is a structure within a fluidic channel.

25. The method of claim 1 wherein the reaction site is a collection of beads within a fluidic channel.

26. The method of claim 1 wherein the initiator includes one or more nucleotides.

27. The method of claim 1 further including the step of monitoring covalent addition of the selected nucleotide triphosphate.

28. The method of claim 1 wherein the error prone polymerase or template independent DNA polymerase is terminal deoxynucleotide transferase.

29. The method of claim 1 wherein the cations are one or more of $Zn^{+2}$, $Co^{+2}$, $Mg^{+2}$ or $Mn^{+2}$.

30. The method of claim 1 wherein the one or more cations is a divalent cation and the availability of the divalent cation at the reaction site is controlled by pH.

31. The method of claim 1 wherein the one or more cations is a divalent cation and the solubility of the divalent cation is reduced at the inactivating pH.

32. The method of claim 1 wherein the template independent polymerase or error-prone polymerase is terminal nucleotidyl transferase and the divalent ion is $Mg^{+2}$ and the inactivating pH renders $Mg^{+2}$ substantially insoluble.

33. The method of claim 1 wherein the template independent polymerase or error-prone polymerase is terminal nucleotidyl transferase and the divalent ion is Mg$^{+2}$ and the inactivating pH is equal to or more than 11 and the inactivating pH renders Mg$^{+2}$ substantially insoluble.

34. The method of claim 1 wherein the one or more cations is a divalent cation and the solubility of the divalent cation is increased at the activating pH.

35. The method of claim 1 wherein the template independent polymerase or error-prone polymerase is terminal nucleotidyl transferase and the divalent ion is Mg$^{+2}$ and the activating pH renders Mg$^{+2}$ substantially soluble.

36. The method of claim 1 wherein the template independent polymerase or error-prone polymerase is terminal nucleotidyl transferase and the divalent ion is Mg$^{+2}$ and the activating pH is less than 11 and the activating pH renders Mg$^{+2}$ substantially soluble.

37. The method of claim 1 wherein the selected nucleotide is a natural nucleotide or a nucleotide analog.

38. The method of claim 1 wherein the selected nucleotide is a member selected from the group consisting of

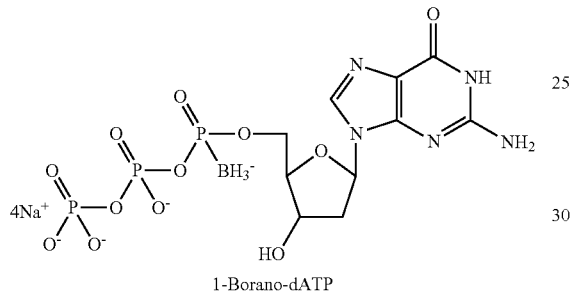
1-Borano-dATP

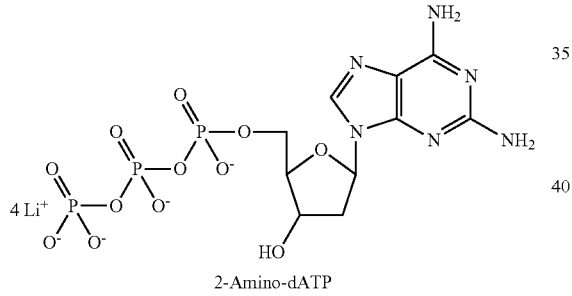
2-Amino-dATP

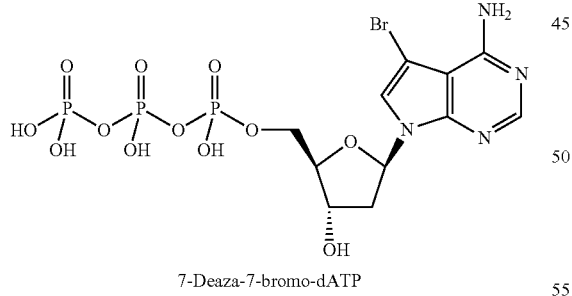
7-Deaza-7-bromo-dATP

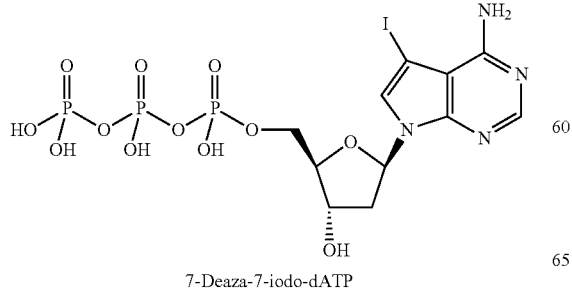
7-Deaza-7-iodo-dATP

-continued

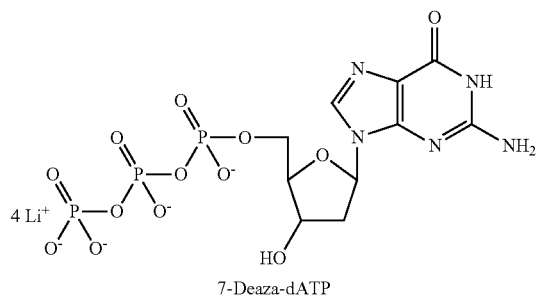
7-Deaza-dATP

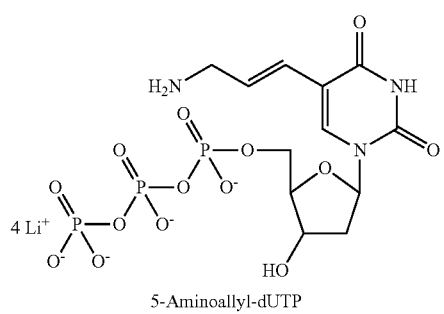
5-Aminoallyl-dUTP

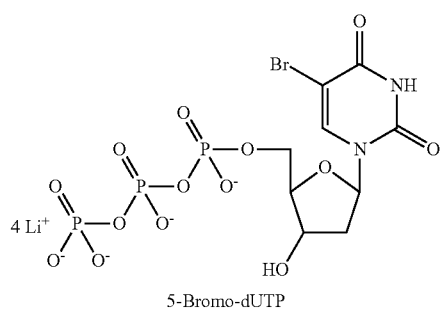
5-Bromo-dUTP

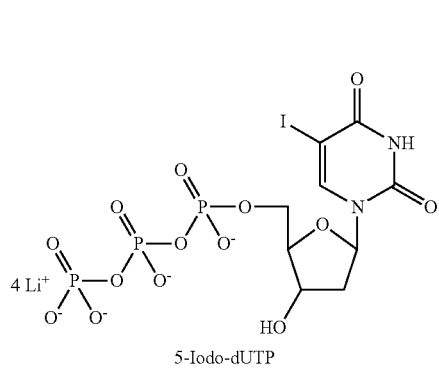
5-Iodo-dUTP

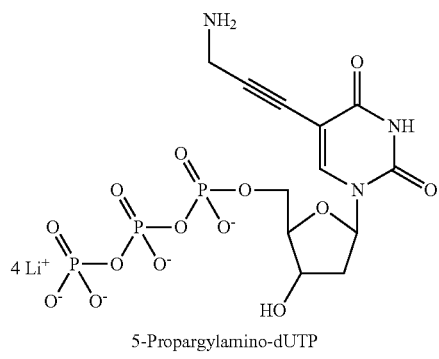
5-Propargylamino-dUTP

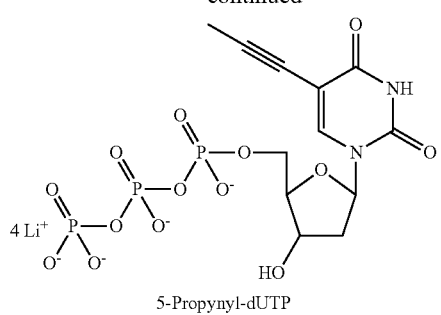
5-Propynyl-dUTP

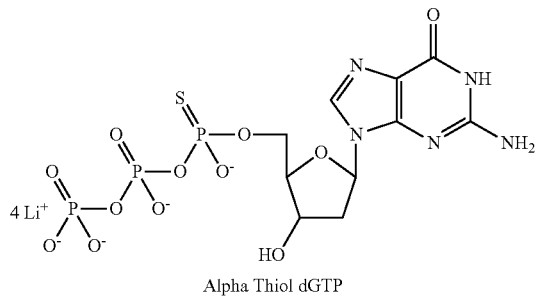
Alpha Thiol dGTP

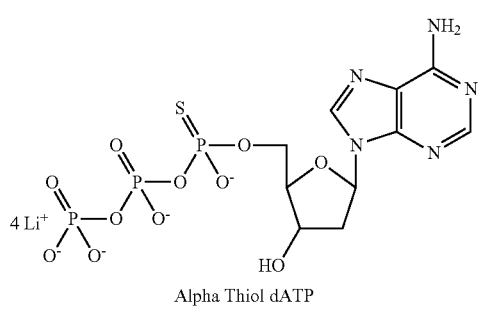
Alpha Thiol dATP

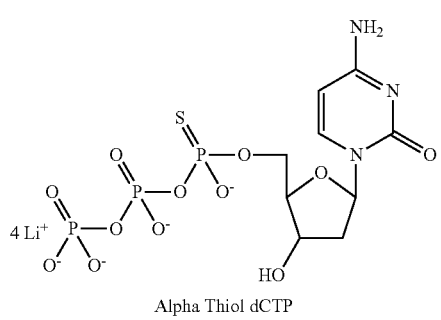
Alpha Thiol dCTP

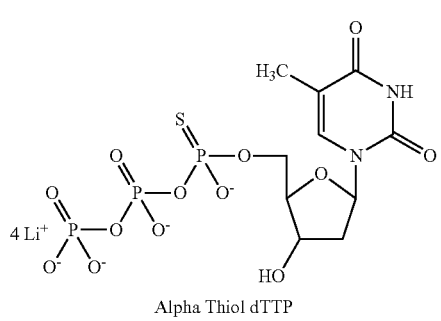
Alpha Thiol dTTP

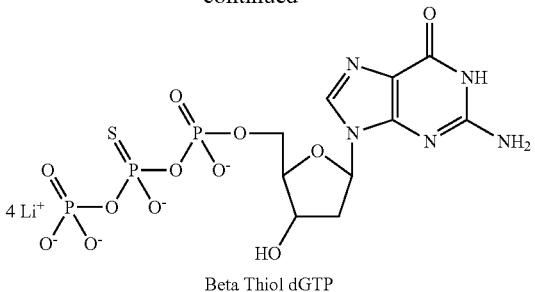
Beta Thiol dGTP

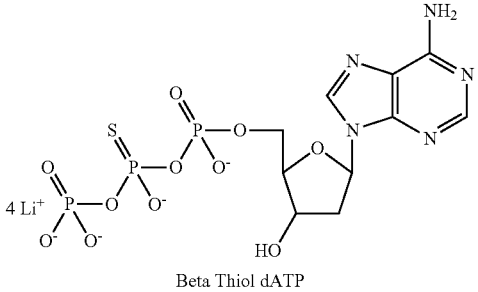
Beta Thiol dATP

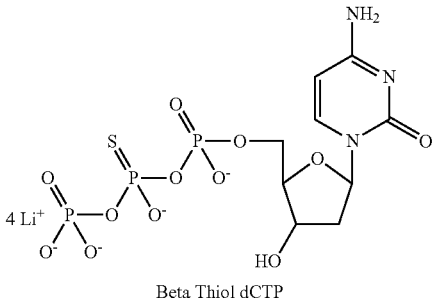
Beta Thiol dCTP

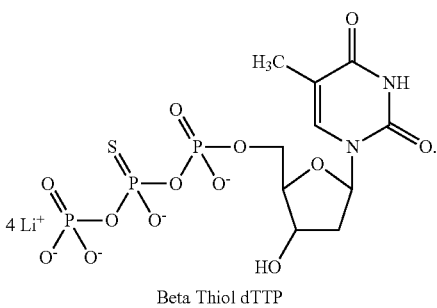
Beta Thiol dTTP

39. The method of claim 1 wherein the initiator is attached by a cleavable moiety.

40. The method of claim 1 further comprising releasing the polynucleotide from the reaction site after the desired sequence of nucleotides has been added to the 3' end of the polynucleotide.

41. The method of claim 1 further comprising releasing the polynucleotide from the reaction site using an enzyme, a chemical, light, or heat.

42. The method of claim 1 further comprising releasing the polynucleotide from the reaction site, collecting the polynucleotide, amplifying the polynucleotide and sequencing the polynucleotide.

43. The method of claim 1 wherein one or more reaction reagents are removed from the reaction site and one or more additional reaction reagents are provided to the reaction site after each round of addition.

44. The method of claim 1 further including a plurality of reaction sites wherein each reaction site is within a reaction zone including an electrode of an electrochemical cell wherein the electrode is an anode or a cathode of the electrochemical cell and wherein addition of a nucleotide triphosphate at each of the plurality of reaction sites is independently controlled by separate application of voltages or currents.

45. The method of claim 1 further including a plurality of reaction sites wherein each reaction site is within a reaction zone including an electrode of an electrochemical cell wherein the electrode is an anode or a cathode of the electrochemical cell and wherein one or more reaction reagents are provided to each of the plurality of reaction sites and a separate voltage or current is applied to the electrochemical cell.

46. The method of claim 1 further including a plurality of reaction sites and a corresponding plurality of reaction zones and electrodes of electrochemical cells wherein reaction at each of the plurality of reaction sites is independently controlled by application of separate voltages or currents to the electrochemical cells.

47. The method of claim 1 further including a plurality of reaction sites and a corresponding plurality of reaction zones and electrodes of electrochemical cells wherein one or more reaction reagents are provided to each of the plurality of reaction sites and reaction at each of the plurality of reaction sites is independently controlled by application of separate voltages or currents to the electrochemical cells.

48. A method for making a plurality of polynucleotides comprising
  (a) combining a selected nucleotide triphosphate, cations, and an error prone polymerase or template independent DNA polymerase in aqueous electrolyte media at a plurality of reaction sites including an initiator sequence attached thereto and having a 3' terminal nucleotide,
  wherein each reaction site is at an inactivating pH that renders the error prone polymerase or template independent DNA polymerase inactive to add the selected nucleotide triphosphate to the initiator sequence, and
  wherein each reaction site is within a corresponding reaction zone including an electrode of a corresponding electrochemical cell wherein the electrode is an anode or a cathode of the electrochemical cell thereby providing a plurality of reaction zones and a plurality of corresponding electrochemical cells;
  (b) applying separate voltages or currents to each of the corresponding electrochemical cells to generate an acid or a base in the aqueous electrolyte media at the corresponding reaction zone to alter pH in the corresponding reaction zone to create an activating pH to activate the error prone polymerase or template independent DNA polymerase,
  wherein reaction reagents are present at selected concentrations and under conditions which covalently add one or more of the selected nucleotide triphosphate to the 3' terminal nucleotide such that the selected nucleotide triphosphate becomes a 3' terminal nucleotide and under conditions wherein a desired number of the selected nucleotide triphosphate is added to the initiator sequence, and
  (c) repeating steps (a) and (b) until the plurality of polynucleotides is formed.

* * * * *